(12) United States Patent
Franklin

(10) Patent No.: US 9,133,241 B2
(45) Date of Patent: Sep. 15, 2015

(54) PEPTIDE COMPOSITIONS

(71) Applicant: TARIX PHARMACEUTICALS LTD., Cambridge, MA (US)

(72) Inventor: Richard Franklin, Cambridge, MA (US)

(73) Assignee: TARIX PHARMACEUTICALS LTD., Cambridge, MA (US)

( * ) Notice: Subject to any disclaimer, the term of this patent is extended or adjusted under 35 U.S.C. 154(b) by 0 days.

(21) Appl. No.: 14/506,497

(22) Filed: Oct. 3, 2014

(65) Prior Publication Data

US 2015/0105335 A1   Apr. 16, 2015

Related U.S. Application Data

(63) Continuation of application No. PCT/US2014/058646, filed on Oct. 1, 2014.

(60) Provisional application No. 61/940,095, filed on Feb. 14, 2014, provisional application No. 61/890,056, filed on Oct. 11, 2013.

(51) Int. Cl.
```
C07K 7/06      (2006.01)
C07K 7/64      (2006.01)
C07K 7/08      (2006.01)
C07K 14/47     (2006.01)
A61K 38/00     (2006.01)
```

(52) U.S. Cl.
CPC ... *C07K 7/06* (2013.01); *C07K 7/08* (2013.01); *C07K 7/64* (2013.01); *C07K 14/47* (2013.01); *A61K 38/00* (2013.01)

(58) Field of Classification Search
CPC ................................. A61K 38/085; C07K 7/14
See application file for complete search history.

(56) References Cited

U.S. PATENT DOCUMENTS

| | | | |
|---|---|---|---|
| 4,244,946 A | 1/1981 | Rivier et al. | |
| 4,305,872 A | 12/1981 | Johnston et al. | |
| 4,316,891 A | 2/1982 | Guillemin et al. | |
| 7,563,862 B2 * | 7/2009 | Sieg et al. | 530/300 |
| 2013/0157942 A1 | 6/2013 | Walensky et al. | |
| 2013/0210726 A1 | 8/2013 | Franklin | |

FOREIGN PATENT DOCUMENTS

| | | |
|---|---|---|
| WO | WO-98/02452 A2 | 1/1998 |
| WO | WO-01/53331 A2 | 7/2001 |
| WO | WO-2004/058807 A2 | 7/2004 |

OTHER PUBLICATIONS

Regenhardt et al. "Cerebroprotective action of angiotensin peptides in stroke," Clinical Science (2014) 126, 195-205.*
NCBI Reference Sequence: WP_008375227.1 "Sensor Histidine Kinase from *Pseudomonas* sp. M47T1" May 28, 2013.*
Altschul, S. and Gish, W., Local alignment statistics, Methods in Enzymology, 266:460-480 (1996).
Banks, William, Characteristics of compounds that cross the blood brain barrier, BMC Neurology, 9(Suppl 1):S3 (2009).
Bodanszky, M. and Sheehan, J. et al., Active esters and resins in peptide synthesis, Chemistry and Industry (London), 38:1597 (1966).
Brady, L. and Dodson, G., Drug design. Reflections on a peptide, Nature 368(6473):692-693 (1994).
Evans, B. et al., Design of nonpeptidal ligands for a peptide receptor: cholecystokinin antagonists, Journal of Medicinal Chemistry, 30(7):1229-1239 (1987).
Fauchere, J. et al., Association with HeLa cells of *Campylobacter jejuni* and *Campylobacter coli* isolated from human feces, Infection and Immunity, 54(2):283-287 (1986).
Gabathuler, Reinhard, Approaches to transport therapeutic drugs across the blood-brain barrier to treat brain diseases, Neurobiology of Disease, 37(1):48-57 (2010).
Galande, A. et al., Understanding base-assisted desulfurization using a variety of disulfide-bridged peptides, Biopolymers, 71(5):534-551 (2003).
GenBank: EIK93378, histidine kinase, Classic [*Pseudomonas* sp. M47T1], retrieved by the Internet—entire document (2012).
Godeny, M. and Sayeski, P., ANG II-induced cell proliferation is dually mediated by c-Src/Yes/Fyn-regulated ERK1/2 activation in the cytoplasm and PKCzeta-controlled ERK1/2 activity within the nucleus, American Journal of Physiology—Cell Physiology, 291(6):C1297-1307 (2006).
Hudson, D. et al., Methionine enkephalin and isosteric analogues. I. Synthesis on a phenolic resin support, International Journal of Peptide Protein Research, 14:177-185 (1979).
International Search Report for PCT/US2014/058646, 6 pages (Mar. 24, 2015).
Jameson, B. et al., A rationally designed CD4 analogue inhibits experimental allergic encephalomyelitis, Nature 368(6473):744-746 (1994).
Koziarz, P. et al., Reciprocal modulation of the binding of angiotensin agonists and antagonists to angiotensin receptors in smooth muscle, General Pharmacology, 24(3):705-713 (1933).
Merrifield, R.B., Solid Phase Peptide Synthesis, Journal of the American Chemical Society, 85:2149-2154 (1963).
Powell, M. et al., Peptide stability in drug development. II. Effect of single amino acid substitution and glycosylation on peptide reactivity in human serum, Pharmaceutical Research, 10(9):1268-1273 (1993).
Proenca, D. et al., Draft Genome Sequence of *Pseudomonas* sp. Strain M47T1, Carried by *Bursaphelenchus xylophilus* Isolated from *Pinus pinaster*, Journal of Bacteriology, 194(17):4789-4790 (2012).
Rizo, J. and Gierasch, L., Constrained peptides: models of bioactive peptides and protein substructures, Annual Review of Biochemistry, 61:387-418 (1992).
Sarr, M. et al., Red wine polyphenols prevent angiotensin II-induced hypertension and endothelial dysfunction in rats: role of NADPH oxidase, Cardiovascular Research, 71(4):794-802 (2006).

(Continued)

*Primary Examiner* — Christina Bradley
(74) *Attorney, Agent, or Firm* — Choate, Hall & Stewart LLP; Fangli Chen; Brian E. Reese

(57) ABSTRACT

The present invention provides, among other things, novel peptides and compositions for treating disease.

7 Claims, 14 Drawing Sheets

(56) References Cited

OTHER PUBLICATIONS

Schmid-Elsaesser, R. et al., A critical reevaluation of the intraluminal thread model of focal cerebral ischemia: evidence of inadvertent premature reperfusion and subarachnoid hemorrhage in rats by laser-Doppler flowmetry, Stroke, 29(10):2162-2170 (1998).

Spatola, A. et al., Structure-activity relationships of enkephalins containing serially replaced thiomethylene amide bond surrogates, Life Sciences, 38(14):1243-1249 (1986).

Stock, Jeff, Signal Transduction: Gyrating histidine kinases, Current Biology, 9(10):R364-R367 (1999).

Vale, W. et al., Characterization of a 41-residue ovine hypothalamic peptide that stimulates secretion of corticotropin and beta-endorphin, Science, 213(4514):1394-1397 (1981).

Wolanin, P. et al., Histidine protein kinases: key signal transducers outside the animal kingdom, Genome Biology, 3(10):3013.1-3013.8 (2002).

Written Opinion for PCT/US2014/058646, 8 pages (Mar. 24, 2015).

\* cited by examiner

HUVEC Cells

HUVEC Cells

HUVEC Cells

HDMEC Cells

HDMEC Cells

HDMEC Cells

HUVEC Cells

SEQUENCE LISTING

```
<160> NUMBER OF SEQ ID NOS: 20

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid, Arg, Lys, Ala, Cit, Orn,
      acetylated Ser, Sar, D-Arg, D-Lys or absent
<220> FEATURE:
<221> NAME/KEY: MOD_RES
<222> LOCATION: (3)..(3)
<223> OTHER INFORMATION: Any amino acid, Val, Ala, Leu, Nle, Ile, Gly,
      Lys, Pro, Aib, Acpc, Tyr or absent
<220> FEATURE:
<221> NAME/KEY: MOD_RES
<222> LOCATION: (5)..(5)
<223> OTHER INFORMATION: Any amino acid, Ile, Ala, Leu, norLeu, Val, Gly
      or absent
<220> FEATURE:
<221> NAME/KEY: MOD_RES
<222> LOCATION: (6)..(6)
<223> OTHER INFORMATION: Any amino acid, His, Arg, 6-NH2-Phe or absent
<220> FEATURE:
<223> OTHER INFORMATION: see specification as filed for detailed
      description of substitutions and preferred embodiments

<400> SEQUENCE: 1

Ala Xaa Xaa Ser Xaa Xaa Cys
1               5
```

```
<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Arg Val Tyr Ile His Pro Phe His
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Arg Val Ser Ile His Cys Phe His
1               5

<210> SEQ ID NO 4
<211> LENGTH: 7
<212> TYPE: PRT
<213> ORGANISM: Unknown
<220> FEATURE:
<223> OTHER INFORMATION: Description of Unknown: Naturally occurring
      Angiotensin (1-7) peptide

<400> SEQUENCE: 4

Asp Arg Val Tyr Ile His Pro
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle

<400> SEQUENCE: 5

Ala Arg Leu Ser Ile His Cys
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(7)
<223> OTHER INFORMATION: Cyclized thioether bridge between positions
<220> FEATURE:
<221> NAME/KEY: MOD_RES
<222> LOCATION: (7)..(7)
<223> OTHER INFORMATION: Any amino acid
```

```
<220> FEATURE:
<223> OTHER INFORMATION: see specification as filed for detailed
      description of substitutions and preferred embodiments

<400> SEQUENCE: 6

Ala Arg Val Xaa Ile His Xaa
1               5

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(7)
<223> OTHER INFORMATION: Cyclized thioether bridge between positions
<220> FEATURE:
<221> NAME/KEY: MOD_RES
<222> LOCATION: (7)..(7)
<223> OTHER INFORMATION: Any amino acid
<220> FEATURE:
<223> OTHER INFORMATION: see specification as filed for detailed
      description of substitutions and preferred embodiments

<400> SEQUENCE: 7

Ala Arg Leu Xaa Ile His Xaa Phe His Leu
1               5                   10

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(7)
<223> OTHER INFORMATION: Cyclized thioether bridge between positions
<220> FEATURE:
<221> NAME/KEY: MOD_RES
<222> LOCATION: (7)..(7)
<223> OTHER INFORMATION: Any amino acid
<220> FEATURE:
<223> OTHER INFORMATION: see specification as filed for detailed
      description of substitutions and preferred embodiments

<400> SEQUENCE: 8

Ala Arg Leu Xaa Ile His Xaa Phe
1               5

<210> SEQ ID NO 9
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Nle
<220> FEATURE:
<221> NAME/KEY: MOD_RES
<222> LOCATION: (3)..(3)
<223> OTHER INFORMATION: Any amino acid
<220> FEATURE:
<221> NAME/KEY: misc_feature
<222> LOCATION: (3)..(6)
<223> OTHER INFORMATION: Cyclized thioether bridge between positions
<220> FEATURE:
<221> NAME/KEY: MOD_RES
<222> LOCATION: (6)..(6)
<223> OTHER INFORMATION: Any amino acid
<220> FEATURE:
<223> OTHER INFORMATION: see specification as filed for detailed
      description of substitutions and preferred embodiments

<400> SEQUENCE: 9

Arg Leu Xaa Ile His Xaa Phe
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (2)..(2)
<223> OTHER INFORMATION: Any amino acid
<220> FEATURE:
<221> NAME/KEY: misc_feature
<222> LOCATION: (2)..(5)
<223> OTHER INFORMATION: Cyclized thioether bridge between positions
<220> FEATURE:
<221> NAME/KEY: MOD_RES
<222> LOCATION: (5)..(5)
<223> OTHER INFORMATION: Any amino acid
<220> FEATURE:
<223> OTHER INFORMATION: see specification as filed for detailed
      description of substitutions and preferred embodiments

<400> SEQUENCE: 10

Leu Xaa Ile His Xaa Phe
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any amino acid
<220> FEATURE:
```

```
<221> NAME/KEY: misc_feature
<222> LOCATION: (4)..(7)
<223> OTHER INFORMATION: Cyclized thioether bridge between positions
<220> FEATURE:
<221> NAME/KEY: MOD_RES
<222> LOCATION: (7)..(7)
<223> OTHER INFORMATION: Any amino acid
<220> FEATURE:
<223> OTHER INFORMATION: see specification as filed for detailed
      description of substitutions and preferred embodiments

<400> SEQUENCE: 11

Ala Arg Leu Xaa Ile His Xaa
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(7)
<223> OTHER INFORMATION: Cyclized thioether bridge between positions
<220> FEATURE:
<221> NAME/KEY: MOD_RES
<222> LOCATION: (7)..(7)
<223> OTHER INFORMATION: Any amino acid
<220> FEATURE:
<223> OTHER INFORMATION: see specification as filed for detailed
      description of substitutions and preferred embodiments

<400> SEQUENCE: 12

Ala Arg Leu Xaa Ile His Xaa Phe His
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any positively-charged amino acid
<220> FEATURE:
<221> NAME/KEY: MOD_RES
<222> LOCATION: (3)..(3)
<223> OTHER INFORMATION: Any aliphatic amino acid
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(7)
<223> OTHER INFORMATION: Cyclized thioether bridge between positions
<220> FEATURE:
<221> NAME/KEY: MOD_RES
<222> LOCATION: (5)..(5)
<223> OTHER INFORMATION: Any aliphatic amino acid
<220> FEATURE:
<221> NAME/KEY: MOD_RES
```

<222> LOCATION: (7)..(7)
<223> OTHER INFORMATION: Any amino acid
<220> FEATURE:
<223> OTHER INFORMATION: see specification as filed for detailed
      description of substitutions and preferred embodiments

<400> SEQUENCE: 13

Ala Xaa Xaa Xaa Xaa His Xaa
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any positively charged amino acid or absent
<220> FEATURE:
<221> NAME/KEY: MOD_RES
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Any amino acid
<220> FEATURE:
<221> NAME/KEY: misc_feature
<222> LOCATION: (4)..(7)
<223> OTHER INFORMATION: Cyclized thioether bridge between positions
<220> FEATURE:
<221> NAME/KEY: MOD_RES
<222> LOCATION: (5)..(5)
<223> OTHER INFORMATION: Any aliphatic amino acid
<220> FEATURE:
<221> NAME/KEY: MOD_RES
<222> LOCATION: (7)..(7)
<223> OTHER INFORMATION: Any amino acid
<220> FEATURE:
<221> NAME/KEY: MOD_RES
<222> LOCATION: (8)..(8)
<223> OTHER INFORMATION: Any amino acid except Pro or absent
<220> FEATURE:
<221> NAME/KEY: MOD_RES
<222> LOCATION: (9)..(9)
<223> OTHER INFORMATION: May or may not be present
<220> FEATURE:
<221> NAME/KEY: MOD_RES
<222> LOCATION: (10)..(10)
<223> OTHER INFORMATION: Any aliphatic residue or absent
<220> FEATURE:
<223> OTHER INFORMATION: see specification as filed for detailed
      description of substitutions and preferred embodiments

<400> SEQUENCE: 14

Ala Xaa Leu Xaa Xaa His Xaa Xaa His Xaa
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (3)..(3)
<223> OTHER INFORMATION: Nle
<220> FEATURE:
<221> NAME/KEY: MOD_RES
<222> LOCATION: (4)..(4)
<223> OTHER INFORMATION: Abu

<400> SEQUENCE: 15

Ala Arg Leu Xaa Ile His Ala
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Nle

<400> SEQUENCE: 16

Ala Arg Leu Ala Ile His Ala
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Arg Val Tyr Ile His Pro
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Arg Val Ser Ile His Cys
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Arg Val Tyr Ile His Pro Phe His
1               5

<210> SEQ ID NO 20
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 20

Asp Arg Val Ser Ile His Cys
1               5
```

PEPTIDE COMPOSITIONS

This application is a continuation of International Application No. PCT/US14/58646, filed Oct. 1, 2014, which claims priority to U.S. provisional patent application No. 61/940,095, filed Feb. 14, 2014, and U.S. provisional patent application No. 61/890,056, filed Oct. 11, 2013 the disclosures of which are hereby incorporated by reference in their entirety.

The instant application contains a Sequence Listing which has been submitted electronically in ASCII format and is hereby incorporated by reference in its entirety. Said ASCII copy, created on Oct. 31, 2014, is named "2009912-0124_SL.txt" and is 9,329 bytes in size. The entire contents of the Sequence Listing are herein incorporated by reference.

BACKGROUND

Biologic medical products are an increasingly common segment of the market for disease therapeutics. Biologic products include, inter alia, vaccines, gene therapy, and natural or recombinant proteins and/or peptides. Biologics can comprise sugars, proteins, nucleic acids, or complex combinations of these substances and have been used as potential therapeutics in a wide variety of diseases, disorders and conditions.

SUMMARY OF THE INVENTION

The present invention provides, among other things, novel peptides compositions comprising provided peptides, and methods for using provided peptides and compositions.

In some embodiments, the present invention provides peptides comprising an amino acid sequence according to formula I $Ala^1$-$Xaa^2$-$Xaa^3$-$Ser^4$-$Xaa^5$-$Xaa^6$-$Cys^7$ (SEQ ID NO: 1). In some embodiments, $Xaa^2$-$Xaa^6$ each may be any amino acid or a peptide bond. In some embodiments, $Xaa^2$ is selected from Arg, Lys, Ala, Cit (citrulline), Orn (ornithine), acetylated Ser, Sar, D-Arg and D-Lys. In some embodiments, $Xaa^3$ is selected from Val, Ala, Leu, Nle, Ile, Gly, Lys, Pro, Aib (2-aminoisobutyric acid), Acpc (1-aminocyclopentane carboxylic acid) and Tyr. In some embodiments, $Xaa^5$ is selected from Ile, Ala, Leu, norLeu, Val and Gly. In some embodiments, $Xaa^6$ is selected from His, Arg and 6-$NH_2$-Phe (6-aminophenylalanine). In some embodiments, the peptide has an amino acid sequence $Ala^1$-$Arg^2$-$Val^3$-$Ser^4$-$Ile^5$-$His^6$-$Cys^7$ (SEQ ID NO: 18). In some embodiments, provided peptides are non-cyclic peptides.

In some embodiments, provided peptides comprise the amino acid sequence $Ala^1$-$Arg^2$-$Val^3$-$Tyr^4$-$Ile^5$-$His^6$-$Pro^7$-$Phe^8$-$His^9$ (SEQ ID NO: 2) or $Ala^1$-$Arg^2$-$Val^3$-$Ser^4$-$Ile^5$-$His^6$-$Cys^7$-$Phe^8$-$His^9$ (SEQ ID NO: 3).

In some embodiments, the peptide is a cyclic peptide. In some embodiments, the cyclic peptide comprises a linkage between amino acids (e.g., between any of the two amino acids). In some embodiments, the linkage is located at residues corresponding to positions $Ser^4$ and $Cys^7$ of SEQ ID NO: 1. In some embodiments, the peptide comprises one or more chemical modifications to increase protease resistance, serum stability, and/or bioavailability.

In some embodiments, the present invention provides compositions comprising one or more peptides according to formula I. In some embodiments, provided compositions comprise a peptide according to formula I and a pharmaceutically acceptable carrier. In some embodiments, the pharmaceutical composition further comprises one or more pharmacologically acceptable excipients selected from a polymer carrier, a disintegration agent, a lubricant, a solvent, or a swelling agent. In some embodiments, the pharmaceutical composition is formulated as a tablet, pill, capsule, granules, a syrup, a spray, an aerosol, a liposomal composition, an ointment, a suppository, an implant, a plaster, or a slow release formulation.

In some embodiments, the pharmaceutical composition is formulated for oral, intramuscular, intravenous, subcutaneous, topical, transdermal, rectal, vaginal, pulmonary, intranasal, intrabuccal, or sublingual administration.

In some embodiments, the present invention provides methods of treating a disease, condition, or disorder including administering to a subject in need thereof one or more peptides according to formula I, or compositions comprising one or more peptides according to formula I.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

DEFINITIONS

Figure 1:
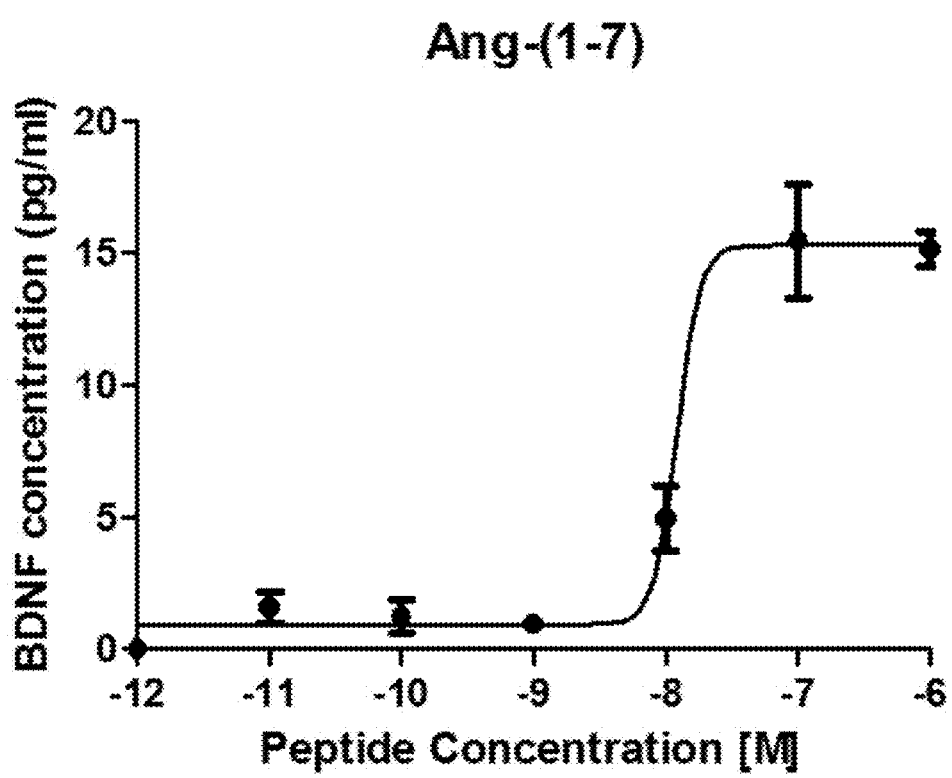
FIG. 1 shows a dose-response curve of angiotensin (1-7) (SEQ ID NO: 4) and the level of BDNF stimulated at each dose in HUVEC.

In order for the present invention to be more readily understood, certain terms are first defined below. Additional definitions for the following terms and other terms are set forth throughout the specification.

Agonist: As used herein, the term "agonist" refers to any molecule that has a positive impact in a function of a protein of interest. In some embodiments, an agonist directly or indirectly enhances, strengthens, activates and/or increases an activity of a protein of interest. In particular embodiments, an agonist directly interacts with the protein of interest. Such agonists can be, e.g., proteins, chemical compounds, small molecules, nucleic acids, antibodies, drugs, ligands, or other agents.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a peptide is biologically active, a portion of that peptide that shares at least one biological activity of the peptide is typically referred to as a "biologically active" portion. In certain embodiments, a peptide has no intrinsic biological activity but that inhibits the effects of one or more naturally-occurring angiotensin compounds is considered to be biologically active.

Carrier or diluent: As used herein, the terms "carrier" and "diluent" refers to a pharmaceutically acceptable (e.g., safe and non-toxic for administration to a human) carrier or diluting substance useful for the preparation of a pharmaceutical formulation. Exemplary diluents include sterile water, bacteriostatic water for injection (BWFI), a pH buffered solution (e.g. phosphate-buffered saline), sterile saline solution, Ringer's solution or dextrose solution.

Dosage form: As used herein, the terms "dosage form" and "unit dosage form" refer to a physically discrete unit of a therapeutic agent for the patient to be treated. Each unit contains a predetermined quantity of active material calculated to produce the desired therapeutic effect. It will be understood, however, that the total dosage of the composition will be decided by the attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, the therapeutic agent is administered continuously over a predetermined period. In some embodiments, the therapeutic agent is administered once a day (QD) or twice a day (BID).

Functional equivalent or derivative: As used herein, the term "functional equivalent" or "functional derivative" denotes a molecule that retains a biological activity (either function or structural) that is substantially similar to that of the original sequence. A functional derivative or equivalent may be a natural derivative or is prepared synthetically. Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include, similarities in charge, bulkiness, hydrophobicity, hydrophilicity, and the like.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control individual (or multiple control individuals) in the absence of the treatment described herein. A "control individual" is an individual afflicted with the same form of disease as the individual being treated, who is about the same age as the individual being treated (to ensure that the stages of the disease in the treated individual and the control individual(s) are comparable).

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Prevent: As used herein, the term "prevent" or "prevention", when used in connection with the occurrence of a disease, disorder, and/or condition, refers to reducing the risk of developing the disease, disorder and/or condition. See the definition of "risk."

Polypeptide: The term "polypeptide" as used herein refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Risk: As will be understood from context, a "risk" of a disease, disorder, and/or condition comprises a likelihood that a particular individual will develop a disease, disorder, and/or condition (e.g., Huntington's Disease, Rett Syndrome, or stroke). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., Huntington's Disease, Rett Syndrome, or stroke). In some embodiments a reference sample or group of reference samples are from individuals comparable to a particular individual. In some embodiments, relative risk is 0, 1, 2, 3, 4, 5, 6, 7, 8, 9, 10, or more.

Stability: As used herein, the term "stable" refers to the ability of the therapeutic agent to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In certain embodiments, pharmaceutical compositions described herein have been formulated such that they are capable of stabilizing, or alternatively slowing or preventing the degradation, of one or more therapeutic agents formulated therewith. In the context of a formulation a stable formulation is one in which the therapeutic agent therein essentially retains its physical and/or chemical integrity and biological activity upon storage and during processes (such as freeze/thaw, mechanical mixing and lyophilization).

Subject: As used herein, the term "subject" refers to a human or any non-human animal (e.g., mouse, rat, rabbit, dog, cat, cattle, swine, sheep, horse or primate). A human includes pre and post natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, condition, or event may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, condition, and/or event (5) having undergone, planning to undergo, or requiring a transplant. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION OF CERTAIN EMBODIMENTS

The present invention provides, among other things, novel peptides, compositions including one or more of those peptides, and methods for treating or reducing risk of one or more diseases, disorders and/or conditions including administration of provided peptides and/or compositions.

Various aspects of the invention are described in detail in the following sections. The use of sections is not meant to limit the invention. Each section can apply to any aspect of the invention. In this application, the use of "or" means "and/or" unless stated otherwise.

Provided Peptides

As used herein, "peptide" and "polypeptide" are interchangeable terms and refer to two or more amino acids bound together by a peptide bond. As used herein, the terms "peptide" and "polypeptide" include both non-cyclic (e.g., linear) and cyclic peptides.

In some embodiments, the present invention provides polypeptides comprising an amino acid sequence according to formula I:

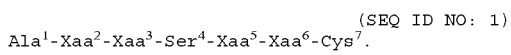

(SEQ ID NO: 1)
$Ala^1$-$Xaa^2$-$Xaa^3$-$Ser^4$-$Xaa^5$-$Xaa^6$-$Cys^7$.

In some embodiments, $Xaa^2$-$Xaa^6$ each may be any amino acid or a peptide bond. In some embodiments, $Xaa^2$ is selected from Arg, Lys, Ala, Cit (citrulline), Orn (ornithine), acetylated Ser, Sar, D-Arg and D-Lys; $Xaa^3$ is selected from Val, Ala, Leu, Nle, Ile, Gly, Lys, Pro, Aib (2-aminoisobutyric acid), Acpc (1-aminocyclopentane carboxylic acid) and Tyr; $Xaa^5$ is selected from Ile, Ala, Leu, norLeu, Val and Gly; and $Xaa^6$ is selected from His, Arg and 6-NH2-Phe (6-aminophenylalanine).

In some embodiments, the present invention provides a peptide comprising the amino acid sequence $Ala^1$-$Arg^2$-$Val^3$-$Ser^4$-$Ile^5$-$His^6$-$Cys^7$ (SEQ ID NO: 18).

In some embodiments, provided peptides are ligands for Mas receptors. Mas receptors are G-protein coupled receptor containing seven transmembrane spanning regions. As used herein, the term "angiotensin-(1-7) receptor" encompasses the G Protein-Coupled Mas Receptors.

Functional Equivalents, Analogs or Derivatives

In some embodiments, a provided peptide is a functional equivalent of a peptide according to formula I. As used herein, a functional equivalent of a peptide according to formula I refers to any peptide that shares amino acid sequence identity to a peptide according to formula I and retains substantially the same or similar activity as the reference peptide. For example, in some embodiments, a functional equivalent of a peptide according to formula I as described herein has brain-derived neurotrophic factor (BDNF) stimulating activity as determined using methods described herein or known in the art. In some embodiments, a functional equivalent of a peptide according to formula I as described herein can bind to or activate an angiotensin-(1-7) receptor (e.g., the G protein-coupled Mas receptor) as determined using various assays described herein or known in the art. In some embodiments, a provided peptide is a non-cyclic peptide.

Typically, a functional equivalent of a peptide according to formula I contains a sequence that includes at least 3 (e.g., at least 4, at least 5, at least 6, at least 7) amino acids from the amino acids that appear in the reference peptide, wherein the at least 3 (e.g., at least 4, at least 5, at least 6, or at least 7) amino acids maintain their relative positions and/or spacing as they appear in the reference peptide. In some embodiments, the reference peptide is naturally-occurring Ang-(1-7), $Asp'^1$-$Arg^2$-$Val^3$-$Tyr^4$-$Ile^5$-$His^6$-$Pro^7$ (SEQ ID NO: 4).

In some embodiments, a functional equivalent of a peptide according to formula I also encompasses any peptide that contains a sequence at least 50% (e.g., at least 60%, 70%, 80%, or 90%) identical to the amino acid sequence of the reference peptide. Percentage of amino acid sequence identity can be determined by alignment of amino acid sequences. Alignment of amino acid sequences can be achieved in various ways that are within the skill in the art, for instance, using publicly available computer software such as BLAST, ALIGN or Megalign (DNASTAR) software. Those skilled in the art can determine appropriate parameters for measuring alignment, including any algorithms needed to achieve maximal alignment over the full length of the sequences being compared. Preferably, the WU-BLAST-2 software is used to determine amino acid sequence identity (Altschul et al., *Methods in Enzymology* 266, 460-480 (1996); http://blast.wustl/edu/blast/README.html). WU-BLAST-2 uses several search parameters, most of which are set to the default values. The adjustable parameters are set with the following values: overlap span=1, overlap fraction=0.125, word threshold (T)=11. HSP score (S) and HSP S2 parameters are dynamic values and are established by the program itself, depending upon the composition of the particular sequence, however, the minimum values may be adjusted and are set as indicated above.

In some embodiments, a functional equivalent, analogue or derivative of a peptide according to formula I is a fragment of the reference peptide. In some embodiments, a functional equivalent, analogue or derivative of a peptide according to formula I contains amino acid substitutions, deletions and/or insertions as compared to the reference peptide. In some embodiments, functional equivalents, analogues or derivatives can be made by altering the amino acid sequences by substitutions, additions, and/or deletions. For example, one or more amino acid residues within the sequence of $Ala^1$-$Arg^2$-$Val^3$-$Ser^4$-$Ile^5$-$His^6$-$Cys^7$ (SEQ ID NO: 18) can be substituted by another amino acid of a similar polarity, which acts as a functional equivalent, resulting in a silent alteration. Substitution for an amino acid within the sequence may be selected from other members of the class to which the amino acid belongs. For example, the positively charged (basic) amino acids include arginine, lysine, and histidine. The nonpolar (hydrophobic) amino acids include leucine, isoleucine, alanine, phenylalanine, valine, proline, tryptophan, and methionine. The uncharged polar amino acids include serine, threonine, cysteine, tyrosine, asparagine, and glutamine. The negatively charged (acid) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions. For example, the amino acid sequence of a peptide inhibitor can be modified or substituted.

Examples of functional equivalents, analogues and derivatives of a peptide according to formula I are described in the section entitled "Exemplary Peptides" below.

According to various embodiments, a provided peptide can be of any length. In some embodiments, a peptide according to the present invention can contain, for example, from 5-50 or 5-25 amino acid residues, such as 5-20, 5-15 or 5-10 amino acid residues. In some embodiments, a peptide according to the present invention contain 5, 6, 7, 8, 9, 10, 11, 12, 13, 14, 15, 16, 17, 18, 19, 20, 21, 22, 23, 24, 25, 30, 35, 40, 45 or 50 residues.

In some embodiments, a peptide according to formula I contains one or more modifications to increase protease resistance, serum stability and/or bioavailability. In some embodiments, suitable modifications are selected from pegylation, acetylation, glycosylation, biotinylation, substitution with D-amino acid and/or un-natural amino acid, and/or cyclization of the peptide.

As used herein, the term "amino acid," in its broadest sense, refers to any compound and/or substance that can be incorporated into a polypeptide chain. In certain embodiments, an amino acid has the general structure $H_2N-C(H)(R)-COOH$. In certain embodiments, an amino acid is a naturally-occurring amino acid. In certain embodiments, an amino acid is a synthetic or un-natural amino acid (e.g., α,α-disubstituted amino acids, N-alkyl amino acids); in some embodiments, an amino acid is a D-amino acid; in certain embodiments, an amino acid is an L-amino acid. "Standard amino acid" refers to any of the twenty standard amino acids commonly found in naturally occurring peptides including both L- and D-amino acids which are both incorporated in peptides in nature. "Nonstandard" or "unconventional amino acid" refers to any amino acid, other than the standard amino acids, regardless of whether it is prepared synthetically or obtained from a natural source. As used herein, "synthetic or un-natural amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, and/or substitution with other chemical groups that can change the peptide's circulating half-life without adversely affecting its activity. Examples of unconventional or un-natural amino acids include, but are not limited to, citrulline, ornithine, norleucine, norvaline, 4-(E)-butenyl-4 (R)-methyl-N-methylthreonine (MeBmt), N-methyl-leucine (MeLeu), aminoisobutyric acid, statine, and N-methyl-alanine (MeAla). Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

In certain embodiments, a peptide according to formula I contains one or more L-amino acids, D-amino acids, and/or un-natural amino acids.

In addition to peptides containing only naturally occurring amino acids, peptidomimetics or peptide analogs are also encompassed by the present invention. Peptide analogs are commonly used in the pharmaceutical industry as non-peptide drugs with properties analogous to those of the template peptide. The non-peptide compounds are termed "peptide mimetics" or peptidomimetics (Fauchere et al., *Infect. Immun.* 54:283-287 (1986); Evans et al., *J. Med. Chem.* 30:1229-1239 (1987)). Peptide mimetics that are structurally related to therapeutically useful peptides and may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as —CH$_2$NH—, —CH$_2$S—, —CH$_2$—CH$_2$—, —CH═CH— (cis and trans), —CH$_2$SO—, —CH(OH)CH$_2$—, —COCH$_2$— etc., by methods well known in the art (Spatola, Peptide Backbone Modifications, Vega Data, 1(3):267 (1983); Spatola et al. *Life Sci.* 38:1243-1249 (1986); Hudson et al. *Int. J. Pept. Res.* 14:177-185 (1979); and Weinstein. B., 1983, Chemistry and Biochemistry, of Amino Acids, Peptides and Proteins, Weinstein eds, Marcel Dekker, New-York). Such peptide mimetics may have significant advantages over naturally-occurring polypeptides including more economical production, greater chemical stability, enhanced pharmacological properties (e.g., half-life, absorption, potency, efficiency, etc.), reduced antigenicity and others.

Provided peptides also include other types of peptide derivatives containing additional chemical moieties not normally part of the peptide, provided that the derivative retains the desired functional activity of the peptide. Examples of such derivatives include (1) N-acyl derivatives of the amino terminal or of another free amino group, wherein the acyl group may be an alkanoyl group (e.g., acetyl, hexanoyl, octanoyl) an aroyl group (e.g., benzoyl) or a blocking group such as F-moc (fluorenylmethyl-O—CO—); (2) esters of the carboxy terminal or of another free carboxy or hydroxyl group; (3) amide of the carboxy-terminal or of another free carboxyl group produced by reaction with ammonia or with a suitable amine; (4) phosphorylated derivatives; (5) derivatives conjugated to an antibody or other biological ligand and other types of derivatives; and (6) derivatives conjugated to a polyethylene glycol (PEG) chain.

Provided peptides may be obtained by any method of peptide synthesis known to those skilled in the art, including synthetic (e.g., exclusive solid phase synthesis, partial solid phase synthesis, fragment condensation, classical solution synthesis, native-chemical ligation) and recombinant techniques. For example, the peptides or peptides derivatives can be obtained by solid phase peptide synthesis, which in brief, consist of coupling the carboxyl group of the C-terminal amino acid to a resin (e.g., benzhydrylamine resin, chloromethylated resin, hydroxymethyl resin) and successively adding N-alpha protected amino acids. The protecting groups may be any such groups known in the art. Before each new amino acid is added to the growing chain, the protecting group of the previous amino acid added to the chain is removed. Such solid phase synthesis has been disclosed, for example, by Merrifield, *J. Am. Chem. Soc.* 85: 2149 (1964); Vale et al., *Science* 213:1394-1397 (1981), in U.S. Pat. Nos. 4,305,872 and 4,316,891, Bodonsky et al. *Chem. Ind.* (London), 38:1597 (1966); and Pietta and Marshall, *Chem. Comm.* 650 (1970) by techniques reviewed in Lubell et al. "Peptides" Science of Synthesis 21.11, *Chemistry of Amides*. Thieme, Stuttgart, 713-809 (2005). The coupling of amino acids to appropriate resins is also well known in the art and has been disclosed in U.S. Pat. No. 4,244,946. (Reviewed in Houver-Weyl, *Methods of Organic Chemistry*. Vol E22a. Synthesis of Peptides and Peptidomimetics, Murray Goodman, Editor-in-Chief, Thieme. Stuttgart. New York 2002).

Unless defined otherwise, the scientific and technological terms and nomenclature used herein have the same meaning as commonly understood by a person of ordinary skill to which this invention pertains. Generally, the procedures of cell cultures, infection, molecular biology methods and the like are common methods used in the art. Such standard techniques can be found in reference manuals such as, for example, Ausubel et al., *Current Protocols in Molecular Biology*, Wiley Interscience, New York, 2001; and Sambrook et al., *Molecular Cloning: A Laboratory Manual*, 3$^{rd}$ edition, Cold Spring Harbor Laboratory Press, N.Y., 2001.

During any process of the preparation of a provided peptide, it may be desirable to protect sensitive reactive groups on any of the molecule concerned. This may be achieved by means of conventional protecting groups such as those described in Protective Groups In Organic Synthesis by T. W. Greene & P. G. M. Wuts, 1991, John Wiley and Sons, New-York; and Peptides: chemistry and Biology by Sewald and Jakubke, 2002, Wiley-VCH, Wheinheim p. 142. For example, alpha amino protecting groups include acyl type protecting groups (e.g., trifluoroacetyl, formyl, acetyl), aliphatic urethane protecting groups (e.g., t-butyloxycarbonyl (BOC), cyclohexyloxycarbonyl), aromatic urethane type protecting groups (e.g., fluorenyl-9-methoxy-carbonyl (Fmoc), benzyloxycarbonyl (Cbz), Cbz derivatives) and alkyl type protecting groups (e.g., triphenyl methyl, benzyl). The amino acids side chain protecting groups include benzyl (for Thr and Ser), Cbz (Tyr, Thr, Ser, Arg, Lys), methyl ethyl, cyclohexyl (Asp, His), Boc (Arg, His, Cys) etc. The protecting groups may be removed at a convenient subsequent stage using methods known in the art.

Further, provided peptides may be synthesized according to the FMOC protocol in an organic phase with protective groups. Desirably, the peptides are purified with a yield of 70% with high-pressure liquid chromatography (HPLC) on a C18 chromatography column and eluted with an acetonitrile gradient of 10-60%. The molecular weight of a peptide can be verified by mass spectrometry (reviewed in Fields, G. B. "Solid-Phase Peptide Synthesis" *Methods in Enzymology*. Vol. 289, Academic Press, 1997).

Alternatively, provided peptides may be prepared in recombinant systems using, for example, polynucleotide sequences encoding the polypeptides. It is understood that a polypeptide may contain more than one of the above-described modifications within the same polypeptide.

While peptides may be effective in eliciting a biological activity in vitro, their effectiveness in vivo might be reduced by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the peptide and require a free N-terminus (Powell et al., *Pharm. Res.* 10:1268-1273 (1993)). In light of this, it is often advantageous to use modified versions of peptides. The modified peptides retain the structural characteristics of the original L-amino acid peptides that confer the desired biological activity of a peptide according to formula I but are advantageously not readily susceptible to cleavage by protease and/or exopeptidases.

Systematic substitution of one or more amino acids of a reference sequence with D-amino acid of the same type (e.g., D-lysine in place of L-lysine) may be used to generate more stable peptides. Thus, a peptide derivative or peptidomimetic of the present invention may be all L, all D or mixed D, L peptide, in either forward or reverse order. The presence of an N-terminal or C-terminal D-amino acid increases the in vivo stability of a peptide since peptidases cannot utilize a D-amino acid as a substrate (Powell et al., *Pharm. Res.* 10:1268-1273 (1993)). Reverse-D peptides are peptides containing D-amino acids, arranged in a reverse sequence relative to a peptide containing L-amino acids. Thus, the C-terminal residue of an L-amino acid peptide becomes N-terminal for the D-amino acid peptide, and so forth. Reverse D-peptides retain the same secondary conformation and therefore similar activity, as the L-amino acid peptides, but are more resistant to enzymatic degradation in vitro and in vivo, and thus can have greater therapeutic efficacy than the original peptide (Brady and Dodson, *Nature* 368:692-693 (1994); Jameson et al., *Nature* 368:744-746 (1994)). Similarly, a reverse-L peptide may be generated using standard methods where the C-terminus of the parent peptide becomes takes the place of the N-terminus of the reverse-L peptide. It is contemplated that reverse L-peptides of L-amino acid peptides that do not have significant secondary structure (e.g., short peptides) retain the same spacing and conformation of the side chains of the L-amino acid peptide and therefore often have the similar activity as the original L-amino acid peptide. Moreover, a reverse peptide may contain a combination of L- and D-amino acids. The spacing between amino acids and the conformation of the side chains may be retained resulting in similar activity as the original L-amino acid peptide.

Another effective approach to confer resistance to peptidases acting on the N-terminal or C-terminal residues of a peptide is to add chemical groups at the peptide termini, such that the modified peptide is no longer a substrate for the peptidase. One such chemical modification is glycosylation of the peptides at either or both termini. Certain chemical modifications, in particular N-terminal glycosylation, have been shown to increase the stability of peptides in human serum (Powell et al., *Pharm. Res.* 10:1268-1273 (1993)). Other chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the present invention includes modified peptides consisting of peptides bearing an N-terminal acetyl group and/or a C-terminal amide group.

Substitution of non-naturally-occurring amino acids for natural amino acids in a subsequence of the peptides can also confer resistance to proteolysis. Such a substitution can, for instance, confer resistance to proteolysis by exopeptidases acting on the N-terminus without affecting biological activity. Examples of non-naturally-occurring amino acids include $\alpha,\alpha$-disubstituted amino acids, N-alkyl amino acids, C-$\alpha$-methyl amino acids, $\beta$-amino acids, and $\beta$-methyl amino acids. Amino acids analogs useful in the present invention may include, but are not limited to, $\beta$-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formyl-methionine, 3-methylhistidine and other unconventional amino acids. Furthermore, the synthesis of peptides with non-naturally-occurring amino acids is routine in the art.

In addition, constrained peptides comprising a reference sequence or a substantially identical reference sequence variation may be generated by methods well known in the art (Rizo and Gierasch, *Ann. Rev. Biochem.* 61:387-418 (1992)). For example, constrained peptides may be generated by adding cysteine residues capable of forming disulfide bridges and, thereby, resulting in a cyclic peptide. Cyclic peptides can be constructed to have no free N- or C-termini. Accordingly, they are not susceptible to proteolysis by exopeptidases, although they may be susceptible to endopeptidases, which do not cleave at peptide termini. The amino acid sequences of the peptides with N-terminal or C-terminal D-amino acids and of the cyclic peptides are usually identical to the sequences of the peptides to which they correspond, except for the presence of N-terminal or C-terminal D-amino acid residue, or their circular structure, respectively.

Cyclic Peptides

In some embodiments, a functional equivalent, analogue or derivative of a peptide according to formula I is a cyclic peptide. As used herein, a cyclic peptide has an intramolecular covalent bond between two non-adjacent residues. The intramolecular bond may be a backbone to backbone, side-chain to backbone or side-chain to side-chain bond (i.e., terminal functional groups of a linear peptide and/or side-chain functional groups of a terminal or interior residue may be linked to achieve cyclization). Typical intramolecular bonds include disulfide, amide and thioether bonds. A variety of means for cyclizing polypeptides are well known in the art, as are many other modifications that can be made to such peptides. For a general discussion, see International Patent Publication Nos. WO 01/53331 and WO 98/02452, the contents of which are incorporated herein by reference. Such cyclic bonds and other modifications can also be applied to the cyclic peptides and derivative compounds of this invention.

Cyclic peptides as described herein may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. Cyclic peptides may also contain one or more rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Suitable derivatives include amino acids having an N-acetyl group (such that the amino group that represents the N-terminus of the linear peptide prior to cyclization is acetylated) and/or a C-terminal amide group (i.e., the carboxy terminus of the linear peptide prior to cyclization is amidated). Residues other than common amino acids that may be present with a cyclic peptide include, but are not limited to, penicillamine, β,β-tetramethylene cysteine, β,β-pentamethylene cysteine, β-mercaptopropionic acid, β,β-pentamethylene-β-mercaptopropionic acid, 2-mercaptobenzene, 2-mercaptoaniline, 2-mercaptoproline, ornithine, diaminobutyric acid, α-aminoadipic acid, m-aminomethylbenzoic acid and α,β-diaminopropionic acid.

Following synthesis of a linear peptide, with or without N-acetylation and/or C-amidation, cyclization may be achieved by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Within further embodiments, cyclization may be achieved by amide bond formation. For example, a peptide bond may be formed between terminal functional groups (i.e., the amino and carboxy termini of a linear peptide prior to cyclization). Within another such embodiment, the linear peptide comprises a D-amino acid. Alternatively, cyclization may be accomplished by linking one terminus and a residue side chain or using two side chains, with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate. Methods for forming amide bonds are generally well known in the art. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. Alternatively, cyclization can be performed using the azide method, in which a reactive azide intermediate is generated from an alkyl ester via a hydrazide. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF.

Exemplary Peptides

Linear Peptides

In certain aspects, the invention provides non-cyclic (e.g., linear) peptides. As discussed above, provided peptides, in various embodiments, comprise an amino acid according to formula I:

(SEQ ID NO: 1)
$Ala^1-Xaa^2-Xaa^3-Ser^4-Xaa^5-Xaa^6-Cys^7$ where Xaa may be any amino acid, or a pharmaceutically acceptable salt thereof.

In some embodiments, $Xaa^2$ is Arg, Lys, Ala, Cit (citrulline), Orn (ornithine), acetylated Ser, Sar, D-Arg and D-Lys. In certain embodiments, $Xaa^2$ is a positively-charged amino acid such as Arg or Lys, typically Arg.

In some embodiments, $Xaa^3$ is Val, Ala, Leu, Nle (norleucine), Ile, Gly, Lys, Pro, HydroxyPro (hydroxyproline), Aib (2-aminoisobutyric acid), Acpc or Tyr. In certain embodiments, $Xaa^3$ is an aliphatic amino acid such as Val, Leu, Ile or Nle, typically Val or Nle.

In some embodiments, $Xaa^5$ is Ile, Ala, Leu, norLeu, Val or Gly. In certain embodiments, $Xaa^5$ is an aliphatic amino acid such as Val, Leu, Ile or Nle, typically Ile.

In some embodiments, $Xaa^6$ is His, Arg or 6-$NH_2$-Phe (6-aminophenylalanine) In certain embodiments, $Xaa^6$ is a fully or partially positively-charged amino acid such as Arg or His.

In certain embodiments, one or more of $Xaa^2$-$Xaa^6$ is identical to the corresponding amino acid in naturally-occurring Ang-(1-7) (i.e., $Asp^1-Arg^2-Val^3-Tyr^4-Ile^5-His^6-Pro^7$ (SEQ ID NO: 4)). In certain such embodiments, all but one or two of $Xaa^2$-$Xaa^6$ are identical to the corresponding amino acid in naturally-occurring Ang-(1-7). In other embodiments, all of $Xaa^2$-$Xaa^6$ are identical to the corresponding amino acid in naturally-occurring Ang-(1-7).

In certain embodiments, $Xaa^3$ is Nle. When $Xaa^3$ is Nle, one or more of $Xaa^2$ and $Xaa^{5-6}$ are optionally identical to the corresponding amino acid in naturally-occurring Ang-(1-7).

In certain such embodiments, all but one or two of Xaa² and Xaa⁵⁻⁶ are identical to the corresponding amino acid in naturally-occurring Ang-(1-7). In other embodiments, each of Xaa² and Xaa⁵⁻⁶ are identical to the corresponding amino acid in naturally-occurring Ang-(1-7), resulting in the amino acid sequence: Ala¹-Arg²-Nle³-Ser⁴-Ile⁵-His⁶-Cys⁷ (SEQ ID NO: 5). In some embodiments, a linear peptide as described comprises the amino acid sequence Ala¹-Arg²-Val³-Tyr⁴-Ile⁵-His⁶-Pro⁷ (SEQ ID NO: 17).

In some embodiments, a linear angiotensin peptide as described comprises one or more amino acid substitutions, deletions, or additions to Asp¹-Arg²-Val³-Tyr⁴-Ile⁵-His⁶-Pro⁷-Phe⁸-His⁹ (SEQ ID NO: 19), which is identical to the sequence of Ang-(1-9). In certain embodiments, the peptide has the amino acid sequence Ala¹-Arg²-Val³-Ser⁴-Ile⁵-His⁶-Cys⁷-Phe⁸-His⁹ (SEQ ID NO: 3). In some embodiments, the peptide has an amino acid sequence Ala¹-Arg²-Val³-Tyr⁴-Ile⁵-His⁶-Pro⁷-Phe⁸-His⁹ (SEQ ID NO: 2).

In some embodiments, provided linear peptides may comprise the amino acid sequence of any of the cyclic peptides described below (i.e., the amino acid sequence of the linear version of the cyclic peptide without cyclization).

Cyclic Peptides

In certain aspects, the invention provides cyclic peptide analogs according to formula I comprising a linkage, such as between the side chains of amino acids corresponding to positions Ser⁴ and Cys⁷ in formula I. These peptide analogs typically comprise 7 amino acid residues, but can also include a cleavable sequence. As discussed in greater detail below, the invention includes fragments and analogs where one or more amino acids are substituted by another amino acid (including fragments), for example, Ala¹-Arg²-Val³-Ser⁴-Ile⁵-His⁶-Cys⁷ (SEQ ID NO:18), wherein a linkage is formed between Ser⁴ and Cys⁷.

Although the following section describes aspects of the invention in terms of a thioether bond linking residues at the 4- and 7-positions, it should be understood that other linkages (as described above) could replace the thioether bridge and that other residues could be cyclized. A thioether bridge is also referred to as a monosulfide bridge or, in the case of Ala-S-Ala, as a lanthionine bridge. Thioether bridge-containing peptides can be formed by two amino acids having one of the following formulas:

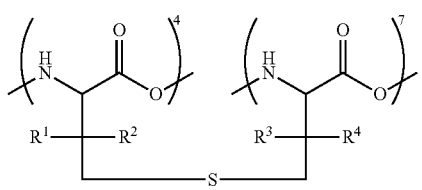

Formula (II)

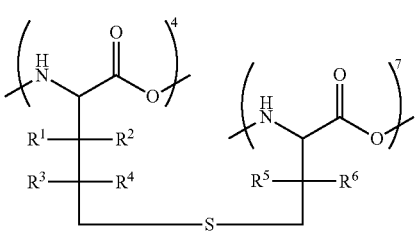

Formula (III)

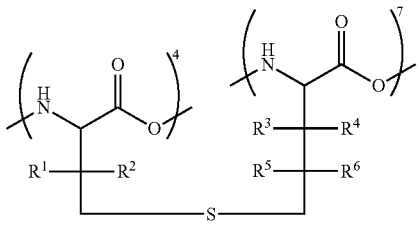

Formula (IV)

In these formulae, $R^1, R^2, R^3, R^4, R^5$ and $R^6$ are independently —H, an alkyl (e.g., $C_1$-$C_6$ alkyl, $C_1$-$C_4$ alkyl) or an aralkyl group, where the alkyl and aralkyl groups are optionally substituted with one or more halogen, —OH or —NRR' groups (where R and R' are independently —H or $C_1$-$C_4$ alkyl). In certain embodiments, R', $R^2$, $R^3$, $R^4$, $R^5$ and $R^6$ are each independently —H or —CH₃, such where all are —H. In some embodiments, provided cyclic peptides do not include a thioether bridge. In some embodiments, provided cyclic peptides do not include a 4,7 thioether bridge.

In certain embodiments, the invention provides a peptide according to formula I, or an analog or derivative thereof, comprising a thioether bridge according to formula (II). Typically, $R^1, R^2, R^3$ and $R^4$ are independently selected from —H and —CH₃. Peptides comprising a thioether bridge according to formula (II) can be produced, for example, by lantibiotic enzymes or by sulfur extrusion of a disulfide. In one example, the disulfide from which the sulfur is extruded can be formed by D-cysteine in position 4 and L-cysteine in position 7 or by D-cysteine in position 4 and L-penicillamine in position 7 (see, e.g., Galande, Trent and Spatola (2003) *Biopolymers* 71, 534-551).

In other embodiments, the linkage of the two amino acids can be the bridges depicted in Formula (III) or Formula (IV). Peptides comprising a thioether bridge according to Formula (III) can be made, for example, by sulfur extrusion of a disulfide formed by D-homocysteine in position 4 and L-cysteine in position 7. Similarly, peptides comprising a thioether bridge as in Formula (IV) can be made, for example, by sulfur extrusion of a disulfide formed by D-cysteine in position 4 and L-homocysteine in position 7.

As discussed above, the peptides of the invention, and analogs and derivatives thereof, vary in length and amino acid composition. In some embodiments, the peptides of the invention preferably have biological activity or are an inactive precursor molecule that can be proteolytically activated (such as how angiotensin (I), with 10 amino acids, is converted to active fragments by cleavage of 2 amino acids). The size of a provided peptide, or analog or derivative thereof, can vary but is typically between from about 5 to 10 amino acids, as long as the "core" pentameric segment comprising the 3-7 thioether-ring structure is encompassed. The amino acid sequence of an analog or derivative of the invention can vary, typically provided that it is biologically active or can become proteolytically activated. Biological activity of an analog or derivative can be determined using methods known in the art, including radioligand binding studies, in vitro cell activation assays and in vivo experiments. See, for example, Godeny and Sayeski, (2006) *Am. J. Physiol. Cell. Physiol.* 291: C1297-1307; Sarr et al., *Cardiovasc. Res.* (2006) 71:794-802; and Koziarz et al., (1933) *Gen. Pharmacol.* 24:705-713.

Provided peptides, or analogs and derivatives thereof, where only the length of the peptide is varied include the following:

a 4,7-cyclized analog designated [Cyc$^{4-7}$], with an amino acid sequence comprising Ala$^1$-Arg$^2$-Val$^3$-Cyc$^4$-Ile$^5$-His$^6$-Cyc$^7$, SEQ ID NO: 6.

a 4,7-cyclized analog designated [Nle$^3$, Cyc$^{4-7}$](1-10), with an amino acid sequence comprising Ala$^1$-Arg$^2$-Nle$^3$-Cyc$^4$-Ile$^5$-His$^6$-Cyc$^7$-Phe$^8$-His$^9$-Leu$^{10}$, SEQ ID NO: 7;

a 4,7-cyclized analog designated [Nle$^3$, Cyc$^{4-7}$](1-8), with an amino acid sequence comprising Ala$^1$-Arg$^2$-Nle$^3$-Cyc$^4$-Ile$^5$-His$^6$-Cyc$^7$-Phe$^8$, SEQ ID NO: 8;

a 4,7-cyclised analog designated [Nle$^3$, Cyc$^{4-7}$](2-8), with an amino acid sequence comprising Arg$^2$-Nle$^3$-Cyc$^4$-Ile$^5$-His$^6$-Cyc$^7$-Phe$^8$, SEQ ID NO: 9;

a 4,7-cyclised analog designated [Nle$^3$, Cyc$^{4-7}$](3-8), with an amino acid sequence comprising Nle$^3$-Cyc$^4$-Ile$^5$-His$^6$-Cyc$^7$-Phe$^8$, SEQ ID NO: 10;

a 4,7-cyclised analog designated [Nle$^3$, Cyc$^{4-7}$](1-7) with an amino acid sequence comprising Ala$^1$-Arg$^2$-Nle$^3$-Cyc$^4$-Ile$^5$-His$^6$-Cyc$^7$, SEQ ID NO: 11; and a 4,7-cyclised analog designated [Nle$^3$, Cyc$^{4-7}$](1-9) with an amino acid sequence comprising Ala$^1$-Arg$^2$-Nle$^3$-Cyc$^4$-Ile$^5$-His$^6$-Cyc$^7$-Phe$^8$-His$^9$, SEQ ID NO: 12.

These analogs can have one of the thioether bridges shown in Formulae (II)-(IV) as the Cyc$^{4-7}$ moiety, for example, where Cyc$^4$ and Cyc$^7$ are represented by Formula (II), such as where R$^1$-R$^4$ are each —H or —CH$_3$, typically —H.

In certain embodiments, a peptide of the invention is represented by Formula (V):

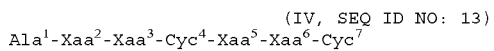

(IV, SEQ ID NO: 13)

Xaa$^2$ is a positively-charged amino acid such as Arg or Lys, typically Arg.

Xaa$^3$ is an aliphatic amino acid, such as Leu, Ile or Val, typically Val.

Cyc$^4$ forms a thioether bridge in conjunction with Cyc$^7$. Cyc$^4$ can be a D-stereoisomer and/or a L-stereoisomer, typically a D-stereoisomer. Examples of Cyc$^4$ (taken with Cyc$^7$) are shown in Formulas (II), (III) and (IV). Typically, the R groups in Formulae (II), (III) and (IV) are —H or —CH$_3$, especially —H.

Xaa$^5$ is an aliphatic amino acid, such as Leu, Ile or Val, typically Ile.

Xaa$^6$ is His.

Cyc$^7$ forms a thioether bridge in conjunction with Cyc$^4$, such as in Formula (II), (III) or (IV). Cyc$^7$ can be a D-stereoisomer and/or a L-stereoisomer, typically a L-stereoisomer. Examples of Cyc$^7$ (taken with Cyc$^4$) are shown in Formulas (II), (III) and (IV). Typically, the R groups in Formulas (II), (III) and (IV) are —H or —CH$_3$, especially —H.

In certain embodiments, one or more of Xaa$^2$-Xaa$^6$ (excluding Cyc$^4$ and Cyc$^7$) is identical to the corresponding amino acid in naturally-occurring Ang-(1-7). In certain such embodiments, all but one or two of Xaa$^2$-Xaa$^6$ are identical to the corresponding amino acid in naturally-occurring Ang-(1-7). In other embodiments, all of Xaa$^2$-Xaa$^6$ are identical to the corresponding amino acid in naturally-occurring Ang-(1-7).

In certain embodiments, Cyc$^4$ and Cyc$^7$ are independently selected from Abu (2-aminobutyric acid) and Ala (alanine), where Ala is present in at least one position. Thus, cyclic analogs can have a thioether linkage formed by -Ala$^4$-S-Ala$^7$- (Formula (II), where R$^1$-R$^4$ are each —H); -Ala$^4$-S-Abu$^7$- (Formula (II): R$^1$-R$^3$ are —H and R$^4$ is —CH$_3$) or -Abu$^4$-S-Ala$^7$- (Formula (II): R$^1$, R$^3$ and R$^4$ are —H and R$^2$ is —CH$_3$). Specific examples of cyclic analogs comprise a -Abu$^4$-S-Ala$^1$- or -Ala$^4$-S-Ala$^7$- linkage.

In certain embodiments, an peptide of the invention is represented by Formula (VI):

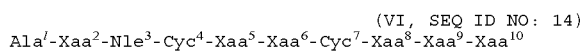

(VI, SEQ ID NO: 14)

As discussed above, one or more of Xaa$^2$, Xaa$^8$, Xaa$^9$ and Xaa$^{10}$ are absent in certain embodiments. For example, (1) Xaa$^{10}$ is absent, (2) Xaa$^9$ and Xaa$^{10}$ are absent, (3) Xaa$^8$, Xaa$^9$ and Xaa$^{10}$ are absent, (4) Xaa$^2$ is absent, (5) Xaa$^2$ and Xaa$^{10}$ are absent, (5) Xaa$^2$, Xaa$^9$ and Xaa$^{10}$ are absent, or (6) Xaa$^2$, Xaa$^8$, Xaa$^9$ and Xaa$^{10}$ are absent. For each of these embodiments, the remaining amino acids have the values described below.

Xaa$^2$, when present, is a positively charged amino acid such as Arg or Lys, typically Arg.

Nle$^3$ is norleucine.

Cyc$^4$ forms a thioether bridge in conjunction with Cyc$^7$. Cyc$^4$ can be a D-stereoisomer and/or a L-stereoisomer, typically a D-stereoisomer. Examples of Cyc$^4$ (taken with Cyc$^7$) are shown in Formulas (II), (III) and (IV). Typically, the R groups in Formulae (II), (III) and (IV) are —H or —CH$_3$, especially —H.

Xaa$^5$ is an aliphatic amino acid, such as Leu, Nle, Ile or Val, typically Ile.

Xaa$^6$ is His.

Cyc$^7$ forms a thioether bridge in conjunction with Cyc$^4$, such as in Formula (II), (III) or (IV). Cyc$^7$ can be a D-stereoisomer and/or a L-stereoisomer, typically a L-stereoisomer. Examples of Cyc$^7$ (taken with Cyc$^4$) are shown in Formulas (II), (III) and (IV). Typically, the R groups in Formulae (II), (III) and (IV) are —H or —CH$_3$, especially —H.

Xaa$^8$, when present, is an amino acid other than Pro, typically Phe or Ile. In certain embodiments, Ile results in an inhibitor of Ang(1-8). In certain embodiments, Phe maintains the biological activity of Ang(1-8) or Ang(1-10).

Xaa$^9$, when present, is His.

Xaa$^{10}$, when present, is an aliphatic residue, for example, Ile, Val or Leu, typically Leu.

In certain embodiments, one or more of Xaa$^2$-Xaa$^{10}$ (excluding Nle$^3$, Cyc$^4$ and Cyc$^7$) is identical to the corresponding amino acid in naturally-occurring Ang (including Ang-(1-7), Ang(1-8), Ang(1-9), Ang(1-10), Ang(2-7), Ang(2-8), Ang(2-9), Ang(2-10), Ang(3-8), Ang(3-9) and Ang(3-10). In certain such embodiments, all but one or two of Xaa$^2$-Xaa$^{10}$ (for those present) are identical to the corresponding amino acid in naturally-occurring Ang. In other embodiments, all of Xaa$^2$-Xaa$^{10}$ (for those present) are identical to the corresponding amino acid in naturally-occurring Ang.

In certain embodiments, Cyc$^4$ and Cyc$^7$ are independently selected from Abu (2-aminobutyric acid) and Ala (alanine), where Ala is present at at least one position. Thus, encompassed are cyclic analogs comprising a thioether linkage formed by -Ala$^4$-S-Ala$^7$- (Formula (II), where R$^1$-R$^4$ are each —H); -Ala$^4$-S-Abu$^7$- (Formula (II): R$^1$-R$^3$ are —H and R$^4$ is —CH$_3$) or -Abu$^4$-S-Ala$^7$- (Formula (II): R$^1$, R$^3$ and R$^4$ are —H and R$^2$ is —CH$_3$). Specific cyclic analogs comprise a -Abu$^4$-S-Ala$^7$- or -Ala$^4$-S-Ala$^7$- linkage.

In some embodiments, the invention provides a peptide, or analog or derivative thereof, with a thioether-bridge between position 4 and position 7 having the amino acid sequence Ala$^1$-Arg$^2$-Nle$^3$-Abu$^4$-Ile$^5$-His$^6$-Ala$^7$ (SEQ ID NO: 15) or the amino acid sequence Ala$^1$-Arg$^2$-Nle$^3$-Ala$^4$-Ile$^5$-His$^6$-Ala$^7$ (SEQ ID NO: 16).

In some embodiments, provided cyclic peptides may be cyclized versions of any of the linear peptides described above.

Pharmaceutical Compositions

In accordance with the methods of the invention, provided peptides, or analogs or derivatives thereof, can be administered to a subject alone (e.g., as a purified peptide or compound), or as a component of a composition or medicament (e.g., in the manufacture of a medicament for the treatment of the disease), as described herein. The compositions can be formulated with a physiologically acceptable carrier or excipient to prepare a pharmaceutical composition. The carrier and composition can be sterile. The formulation should suit the mode of administration. Methods of formulating compositions are known in the art (see, e.g., Remington's Pharmaceuticals Sciences, 17$^{th}$ Edition, Mack Publishing Co., (Alfonso R. Gennaro, editor) (1989)).

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulations can include standard carriers such as pharmaceutical grades of mannitol, lactose, starch, magnesium stearate, polyvinyl pyrrolidone, sodium saccharine, cellulose, magnesium carbonate, etc.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

In some embodiments, provided compositions, including those provided as pharmaceutical formulations, comprise a liquid carrier such as but not limited to water, saline, phosphate buffered saline, Ringer's solution, dextrose solution, serum-containing solutions, Hank's solution, other aqueous physiologically balanced solutions, oils, esters and glycols.

Provided peptides, or analogs or derivatives thereof, as described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Oral Formulations

In some embodiments, a suitable pharmaceutical composition is an oral formulation. It is contemplated that any medically-acceptable oral formulation may be used within the scope of the present invention.

In some embodiments, provided compositions include at least one pH-lowering agent. It is contemplated that a pH-lowering agent suitable for use in some embodiments of the present invention include any pharmaceutically acceptable pH-lowering agent, or combination of pH-lowering agents, that a) are not toxic to the gastrointestinal tract, b) are capable of either delivering hydrogen ions or capable of inducing higher hydrogen ion content from the local environment, and/or c) that are capable of being orally administered in an amount sufficient to lower the local intestinal pH below the pH optima for proteases found there. Various tests may be used to determine if a pH-lowering agent is suitable for the present invention and what amount is appropriate. For example, a pH-lowering agent or combination of pH-lowering agents is suitable for the present invention if a particular amount, when added to a solution of 10 milliliters of 0.1M sodium bicarbonate lowers the pH of the solution to no higher than 5.5, 4.7, or 3.5. In some embodiments, an amount of pH-lowering agent or agents may be added to lower pH, in a solution of 10 milliliters of 0.1M sodium bicarbonate, to no higher than 3.4, 3.2, 3.0, or 2.8.

In some embodiments, a suitable pH-lowering agent or agents include at least one pH-lowering agent that has a pKa no higher than 4.2 (e.g., no higher than 4.0, 3.8, 3.6, 3.4, 3.2, 3.0 or 2.8). Exemplary pH-lowering agents suitable for the present invention include, but are not limited to, carboxylic acids such as acetylsalicylic, acetic, ascorbic, citric, fumaric, glucuronic, glutaric, glyceric, glycocolic, glyoxylic, isocitric, isovaleric, lactic, maleic, oxaloacetic, oxalosuccinic, propionic, pyruvic, succinic, tartaric, and valeric; aluminum chloride; zinc chloride; acid salts of amino acids (or derivatives thereof) including acid salts of acetylglutamic acid, alanine, arginine, asparagine, aspartic acid, betaine, carnitine, carnosine, citrulline, creatine, glutamic acid, glycine, histidine, hydroxylysine, hydroxyproline, hypotaurine, isoleucine, leucine, lysine, methylhistidine, norleucine, ornithine, phenylalanine, proline, sarcosine, serine, taurine, threonine, tryptophan, tyrosine, and valine; certain phosphate esters including fructose 1,6 diphosphate and glucose 1,6 diphosphate may also be appropriate pH-lowering agents in certain embodiments. In particular embodiments, citric acid or tartaric acid is used as pH-lowering agent.

The quantity required of any particular pH-lowering agent or combination of pH-lowering agents may vary. Typically, a suitable amount may be determined using various tests known in the art and described herein (for example, using pH-lowering test in a solution of 10 milliliters of 0.1M sodium bicarbonate described above). As non-limiting examples, suitable amount of a pH lowering agent used in a formulation according to the present invention may be an amount of or greater than about 100 mg, 200 mg, 250 mg, 300 mg, 350 mg, 400 mg, 425 mg, 450 mg, 475 mg, 500 mg, 525 mg, 550 mg, 575 mg, 600 mg, 625 mg, 650 mg, 675, mg, 700 mg, 725 mg, 750 mg, 775 mg, 800 mg, 825 mg, 850 mg, 875 mg, 900 mg, 925 mg, 950 mg, 975 mg, or 1,000 mg. In other embodiments, the amount of citric acid used may exceed 1,000 mg.

In some embodiments, a suitable amount of a pH lowering agent (e.g., citric acid or tartaric acid) used may be measured as a percent of the total weight of a particular dosage form. As non-limiting examples, a suitable amount of a pH lowering agent used may be an amount of or greater than about 10% (e.g., of or greater than 15%, 20%, 25%, 30%, 35%, 40%, 45%, 50%, 55%, 60%, 65%, 70%, 75%, 80%, 85%, 90%, or 95%) of the total weight of a solid dosage form.

In various embodiments, a composition of the invention includes one or more absorption enhancers. As used herein, an absorption enhancer refers to an agent that increase the solubility of other components in either the aqueous or lipophilic environment into which they are released and/or enhance the uptake of an active peptide (e.g., a linear or cyclized peptide according to formula I) across the intestinal wall. In some embodiments, an absorption enhancer is referred to as a solubility enhancer and/or an uptake enhancer.

In some embodiments, it is possible to have a mixture of absorption enhancers wherein some provide enhanced solubility, some provide enhanced uptake, and some provide both. It is possible to have various numbers of absorption enhancers in a given embodiment including, without limitation, one, two, three, four, five, six, seven, eight, nine, or ten absorption enhancers.

Surface active agents are an example of useful absorption enhancers with properties of both solubility enhancers and uptake enhancers. In some embodiments, when surface active agents are used as absorption enhancers, they may be free flowing powders for facilitating the mixing and loading of capsules during the manufacturing process. In other embodiments when a surface active agent is used to increase the bioavailability of a provided peptide, the surface active agent may be selected from the group consisting of (a) anionic surface active agents such as cholesterol derivatives (e.g. bile acids), (b) cationic surface agents (e.g. acyl carnitines, phospholipids and the like), (c) non-ionic surface active agents, and (d) mixtures of anionic surface active agents and negative charge neutralizers, and combinations thereof. Negative charge neutralizers include but are not limited to acyl carnitines, cetyl pyridinum chloride, and the like.

In some embodiments, an acid soluble bile acid and a cationic surface active agent with be used together as absorption enhancers. Acyl carnitines (such as lauroyl carnitine), phospholipids and bile acids may be particularly effective absorption enhancers in some embodiments.

While a variety of absorption enhancers are suitable for use in various embodiments, the following exemplary list is intended to illustrate some embodiments of the present invention. Without limitation, some suitable absorption enhancers include: (a) salicylates such as sodium salicylate, 3-methoxysalicylate, 5-methoxysalicylate and homovanilate; (b) bile acids such as taurocholic, tauorodeoxycholic, deoxycholic, cholic, glycholic, lithocholate, chenodeoxycholic, ursodeoxycholic, ursocholic, dehydrocholic, fusidic, etc.; (c) non-ionic surfactants such as polyoxyethylene ethers (e.g. Brij 36T, Brij 52, Brij 56, Brij 76, Brij 96, Texaphor A6, Texaphor A14, Texaphor A60 etc.), p-t-octyl phenol polyoxyethylenes (Triton X-45, Triton X-100, Triton X-114, Triton X-305 etc.) nonylphenoxypoloxyethylenes (e.g. Igepal CO series), polyoxyethylene sorbitan esters (e.g. Tween-20, Tween-80 etc.); (d) anionic surfactants such as dioctyl sodium sulfosuccinate; (e) lyso-phospholipids such as lysolecithin and lysophosphatidylethanolamine; (f) acylcarnitines, acylcholines and acyl amino acids such as lauroylcarnitine, myristoylcarnitine, palmitoylcarnitine, lauroylcholine, myristoylcholine, palmitoylcholine, hexadecyllysine, N-acylphenylalanine, N-acylglycine etc.; g) water soluble phospholipids such as diheptanoylphosphatidylcholine, dioctylphosphatidylcholine etc.; (h) medium-chain glycerides which are mixtures of mono-, di- and triglycerides containing medium-chain-length fatty acids (caprylic, capric and lauric acids); (i) ethylene-diamine-tetraacetic acid; (j) cationic surfactants such as cetylpyridinium chloride; (k) fatty acid derivatives of polyethylene glycol such as Labrasol, Labrafac, etc.; and (l) alkylsaccharides such as lauroyl maltoside, lauroyl sucrose, myristoyl sucrose, palmitoyl sucrose, etc.

In some embodiments, the absorption enhancer(s) will be present in a quantity measured as a percent by weight, relative to the overall weight of the pharmaceutical composition (typically exclusive of enteric coating). By way of additional non-limiting example, the quantity of absorption enhancer present in an embodiment may range from 0.1 to 20 percent by weight; from 0.5 to 20 percent by weight; from 1.0 to 20 percent by weight, from 2.0 to 20 percent by weight, from 3.0 to 20 percent by weight, from 4.0 to 20 percent by weight, from from 5.0 to 20 percent by weight, from 5.0 to 15 percent by weight, from 5.0 to 14 percent by weight, from 5.0 to 13 percent by weight, from 5.0 to 12 percent by weight, from 5.0 to 12 percent by weight, from 5.0 to 11 percent by weight, from 5.0 to 10 percent by weight, from 6.0 to 10 percent by weight, from 7.0 to 10 percent by weight, from 8.0 to 10 percent by weight, from 9.0 to 10 percent by weight, from 5.0 to 9.0 percent by weight, from 5.0 to 8.0 percent by weight, from 5.0 to 7.0 percent by weight, and from 5.0 to 6.0 percent by weight.

In some embodiments, the weight ratio of pH-lowering agent(s) to absorption enhancer(s) may be about 3:1, 4:1, 5:1, 6:1, 7:1, 8:1, 9:1, 10:1, 11:1, 12:1, 13:1, 14:1, 15:1, 16:1, 17:1, 18:1, 19:1, 20:1 or between any two of the foregoing exemplary ratios. The total weight of all pH-lowering agents and the total weight of all absorption enhancers in a given pharmaceutical composition is included in the foregoing exemplary ratios. For example, if a pharmaceutical composition includes two pH-lowering agents and three absorption enhancers, the foregoing ratios will be computed on the total combined weight of both pH-lowering agents and the total combined weight of all three absorption enhancers.

In some embodiments, the absorption enhancer(s) will be soluble at acid pH, such as less than pH 5.5, and in particular, between pH 3.0 and pH 5.0.

In some embodiments, provided compositions comprise one or more protective vehicles. As used herein, a protective vehicle refers to any protective component and/or structure, such as a carrier, a layer, a coating or other vehicle, that protects an active peptide (e.g., a linear or cyclic peptide according to formula I) from stomach proteases. Typically, a protective vehicle dissolves eventually so that the active and other ingredients in a particular dosage form may be released. A common form of protective vehicle is an enteric coating. In some embodiments, a suitable enteric costing may prevent breakdown of the pharmaceutical composition of the invention in 0.1N HCl for at least two hours, then capable of permitting complete release of all contents of the pharmaceutical composition within thirty minutes after pH is increased to 6.3 in a dissolution bath in which said composition is rotating at 100 revolutions per minute.

Many enteric coatings are known in the art and are useful in one or more embodiments. Non-limiting examples of enteric coatings include cellulose acetate phthalate, hydroxypropyl methylethylcellulose succinate, hydroxypropyl methylcellulose phthalate, carboxyl methylethylcellulose and methacrylic acid-methyl methacrylate copolymer. In some embodiments, absorption enhancers (such as solubility and/or uptake enhancer(s)), and pH-lowering agent(s), are included in a sufficiently viscous protective syrup to permit protected passage of the components of the embodiment through the stomach.

Suitable enteric coatings may be applied, for example, to capsules after the active and other components of the invention have been loaded within the capsule. In other embodiments, enteric coating is coated on the outside of a tablet or coated on the outer surface of particles of active components which are then pressed into tablet form, or loaded into a capsule.

In some embodiments it may be desirable that all components of the invention be released from the carrier or vehicle, and solubilized in the intestinal environment as simultaneously as possible. It may also be preferred in some embodiments that the vehicle or carrier release the active components in the small intestine where uptake enhancers that increase transcellular or paracellular transport are less likely to cause undesirable side effects than if the same uptake enhancers were later released in the colon. It will be appreciated, however, that the present invention is believed effective in the colon as well as in the small intestine. Numerous vehicles or carriers, in addition to the ones discussed above, are known in the art.

In some embodiments, it may be desirable (especially in optimizing how simultaneously the components of the invention are released) to keep the amount of enteric coating low. In some embodiments, an enteric coating adds no more than 30% to the weight of the remainder of pharmaceutical composition such as a solid dosage form (the "remainder" being the pharmaceutical composition exclusive of enteric coating itself). In other embodiments, an enteric coating adds less than 20%, less than 19%, less than 18%, less than 17%, less than 16%, less than 15%, less than 14%, less than 13%, less than 12%, less than 11%, or less than 10%. In some embodiments, a protective vehicle such as an enteric coating constitutes an amount of or less than approximately 25%, 24%, 23%, 22%, 21%, 20%, 19%, 18%, 17%, 16%, 15%, 14%, 13%, 12%, 11%, 10%, 9%, 8%, 7%, 6%, 5% of the total weight of a pharmaceutical composition (e.g., a solid dosage form).

Dosing

In some embodiments, a composition is administered in a therapeutically effective amount and/or according to a dosing regimen that is correlated with a particular desired outcome (e.g., with treating or reducing risk for disease).

Any peptide according to formula I as described herein (or a composition or medicament containing a peptide according to formula I as described herein) may be administered by any appropriate route. In some embodiments, a peptide according to formula I as described herein is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, a peptide according to formula I as described herein is administered intravenously. In other embodiments, a peptide according to formula I as described herein is administered by direct administration to a target tissue, such as heart or muscle (e.g., intramuscular), tumor (intratumorally), nervous system (e.g., direct injection into the brain; intraventricularly; intrathecally). Alternatively, a peptide according to formula I as described herein (or a composition or medicament containing a peptide described herein) can be administered via inhalation, parenterally, intradermally, transdermally, or transmucosally (e.g., orally or nasally). More than one route can be used concurrently, if desired.

In some embodiments, a peptide according to formula I herein is administered orally. In some embodiments, the present invention provides solid dosage forms of a peptide according to formula I as described herein for oral administration including (a) a peptide according to formula I, (b) at least one pharmaceutically acceptable pH-lowering agent, (c) at least one absorption enhancer effective to promote bioavailability of the peptide according to formula I, and (d) a protective vehicle. In some embodiments, the solid dosage form is a capsule or tablet. Various methods and ingredients for making oral formulations are known in the art and it is expected that one of skill would be able to determine which of these methods and ingredients will be compatible with the invention as described in this specification and/or in PCT Patent Application No. PCT/US13/60139, filed on Sep. 17, 2013, the disclosure of which is hereby incorporated in its entirety. Such methods and ingredients are also contemplated as within the scope of the present invention.

In some embodiments, a composition is administered in a therapeutically effective amount and/or according to a dosing regimen that is correlated with a particular desired outcome (e.g., with treating or reducing risk for disease).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, severity of cardiac defect and/or level of risk of cardiac defect, etc., or combinations thereof). Such doses or amounts can be determined by those of ordinary skill. In some embodiments, an appropriate dose or amount is determined in accordance with standard clinical techniques. For example, in some embodiments, an appropriate dose or amount is a dose or amount sufficient to reduce one or more symptoms by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100% or more. Alternatively or additionally, in some embodiments, an appropriate dose or amount is determined through use of one or more in vitro or in vivo assays to help identify desirable or optimal dosage ranges or amounts to be administered.

In various embodiments, a peptide according to formula I is administered at a therapeutically effective amount. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

Therapeutically effective dosage amounts of peptides according to formula I, including derivatives, analogs, and/or salts may be present in varying amounts in various embodiments. In some embodiments, a therapeutically effective dosage amount can be, for example, about 1-10,000 µg/kg, about 5-1,500 µg/kg, about 100-1,000 µg/kg, or 50-500 µg/kg. In some embodiments, the therapeutically effective dosage amount can be, for example, about 1 µg/kg, 2.5 µg/kg, 5 µg/kg, 10 µg/kg, 20 µg/kg, 30 µg/kg, 40 µg/kg, 50 µg/kg, 60

μg/kg, 70 μg/kg, 80 μg/kg, 90 μg/kg, 100 μg/kg, 150 μg/kg, 200 μg/kg, 250 μg/kg, 300 μg/kg, 400 μg/kg, 500 μg/kg, 600 μg/kg, 700 μg/kg, 800 μg/kg, 900 μg/kg, 1000 μg/kg, or 1500 μg/kg. The effective dose for a particular individual can be varied (e.g., increased or decreased) over time, depending on the needs of the individual. In some embodiments, the therapeutically effective amount described herein is provided in one dose. In some embodiments, the therapeutically effective amount described herein is provided in one day.

In other embodiments, a therapeutically effective dosage amount may be, for example, about 0.001 mg/kg weight to 500 mg/kg weight, e.g., from about 0.001 mg/kg weight to 400 mg/kg weight, from about 0.001 mg/kg weight to 300 mg/kg weight, from about 0.001 mg/kg weight to 200 mg/kg weight, from about 0.001 mg/kg weight to 100 mg/kg weight, from about 0.001 mg/kg weight to 90 mg/kg weight, from about 0.001 mg/kg weight to 80 mg/kg weight, from about 0.001 mg/kg weight to 70 mg/kg weight, from about 0.001 mg/kg weight to 60 mg/kg weight, from about 0.001 mg/kg weight to 50 mg/kg weight, from about 0.001 mg/kg weight to 40 mg/kg weight, from about 0.001 mg/kg weight to 30 mg/kg weight, from about 0.001 mg/kg weight to 25 mg/kg weight, from about 0.001 mg/kg weight to 20 mg/kg weight, from about 0.001 mg/kg weight to 15 mg/kg weight, from about 0.001 mg/kg weight to 10 mg/kg weight. In some embodiments, the therapeutically effective amount described herein is provided in one dose. In some embodiments, the therapeutically effective amount described herein is provided in one day.

In still other embodiments, a therapeutically effective dosage amount may be, for example, about 0.001 mg/kg weight to about 1 mg/kg weight, e.g. from about 0.001 mg/kg weight to about 0.9 mg/kg weight, from about 0.001 mg/kg weight to about 0.8 mg/kg weight, from about 0.001 mg/kg weight to about 0.8 mg/kg weight, from about 0.001 mg/kg weight to about 0.7 mg/kg weight, from about 0.001 mg/kg weight to about 0.6 mg/kg weight, from about 0.001 mg/kg weight to about 0.5 mg/kg weight, from about 0.01 mg/kg weight to about 1 mg/kg weight, from about 0.01 mg/kg weight to about 0.9 mg/kg weight, from about 0.01 mg/kg weight to about 0.8 mg/kg weight, from about 0.01 mg/kg weight to about 0.7 mg/kg weight, from about 0.01 mg/kg weight to about 0.6 mg/kg weight, from about 0.01 mg/kg weight to about 0.5 mg/kg weight, from about 0.02 mg/kg weight to about 1 mg/kg weight, from about 0.02 mg/kg weight to about 0.9 mg/kg weight, from about 0.02 mg/kg weight to about 0.8 mg/kg weight, from about 0.02 mg/kg weight to about 0.7 mg/kg weight, from about 0.02 mg/kg weight to about 0.6 mg/kg weight, from about 0.02 mg/kg weight to about 0.5 mg/kg weight, from about 0.03 mg/kg weight to about 1 mg/kg weight, from about 0.03 mg/kg weight to about 0.9 mg/kg weight, from about 0.03 mg/kg weight to about 0.8 mg/kg weight, from about 0.03 mg/kg weight to about 0.7 mg/kg weight, from about 0.03 mg/kg weight to about 0.6 mg/kg weight, from about 0.03 mg/kg weight to about 0.5 mg/kg weight, from about 0.04 mg/kg weight to about 1 mg/kg weight, from about 0.04 mg/kg weight to about 0.9 mg/kg weight, from about 0.04 mg/kg weight to about 0.8 mg/kg weight, from about 0.04 mg/kg weight to about 0.7 mg/kg weight, from about 0.04 mg/kg weight to about 0.6 mg/kg weight, from about 0.04 mg/kg weight to about 0.5 mg/kg weight, from about 0.05 mg/kg weight to about 1 mg/kg weight, from about 0.05 mg/kg weight to about 0.9 mg/kg weight, from about 0.05 mg/kg weight to about 0.8 mg/kg weight, from about 0.05 mg/kg weight to about 0.7 mg/kg weight, from about 0.05 mg/kg weight to about 0.6 mg/kg weight, from about 0.05 mg/kg weight to about 0.5 mg/kg weight. In some embodiments, the therapeutically effective amount described herein is provided in one dose. In some embodiments, the therapeutically effective amount described herein is provided in one day.

In still other embodiments, a therapeutically effective dosage amount may be, for example, about 0.0001 mg/kg weight to 0.1 mg/kg weight, e.g. from about 0.0001 mg/kg weight to 0.09 mg/kg weight, from about 0.0001 mg/kg weight to 0.08 mg/kg weight, from about 0.0001 mg/kg weight to 0.07 mg/kg weight, from about 0.0001 mg/kg weight to 0.06 mg/kg weight, from about 0.0001 mg/kg weight to 0.05 mg/kg weight, from about 0.0001 mg/kg weight to about 0.04 mg/kg weight, from about 0.0001 mg/kg weight to 0.03 mg/kg weight, from about 0.0001 mg/kg weight to 0.02 mg/kg weight, from about 0.0001 mg/kg weight to 0.019 mg/kg weight, from about 0.0001 mg/kg weight to 0.018 mg/kg weight, from about 0.0001 mg/kg weight to 0.017 mg/kg weight, from about 0.0001 mg/kg weight to 0.016 mg/kg weight, from about 0.0001 mg/kg weight to 0.015 mg/kg weight, from about 0.0001 mg/kg weight to 0.014 mg/kg weight, from about 0.0001 mg/kg weight to 0.013 mg/kg weight, from about 0.0001 mg/kg weight to 0.012 mg/kg weight, from about 0.0001 mg/kg weight to 0.011 mg/kg weight, from about 0.0001 mg/kg weight to 0.01 mg/kg weight, from about 0.0001 mg/kg weight to 0.009 mg/kg weight, from about 0.0001 mg/kg weight to 0.008 mg/kg weight, from about 0.0001 mg/kg weight to 0.007 mg/kg weight, from about 0.0001 mg/kg weight to 0.006 mg/kg weight, from about 0.0001 mg/kg weight to 0.005 mg/kg weight, from about 0.0001 mg/kg weight to 0.004 mg/kg weight, from about 0.0001 mg/kg weight to 0.003 mg/kg weight, from about 0.0001 mg/kg weight to 0.002 mg/kg weight. In some embodiments, the therapeutically effective dose may be 0.0001 mg/kg weight, 0.0002 mg/kg weight, 0.0003 mg/kg weight, 0.0004 mg/kg weight, 0.0005 mg/kg weight, 0.0006 mg/kg weight, 0.0007 mg/kg weight, 0.0008 mg/kg weight, 0.0009 mg/kg weight, 0.001 mg/kg weight, 0.002 mg/kg weight, 0.003 mg/kg weight, 0.004 mg/kg weight, 0.005 mg/kg weight, 0.006 mg/kg weight, 0.007 mg/kg weight, 0.008 mg/kg weight, 0.009 mg/kg weight, 0.01 mg/kg weight, 0.02 mg/kg weight, 0.03 mg/kg weight, 0.04 mg/kg weight, 0.05 mg/kg weight, 0.06 mg/kg weight, 0.07 mg/kg weight, 0.08 mg/kg weight, 0.09 mg/kg weight, or 0.1 mg/kg weight. The effective dose for a particular individual can be varied (e.g., increased or decreased) over time, depending on the needs of the individual. In some embodiments, the therapeutically effective amount described herein is provided in one dose. In some embodiments, the therapeutically effective amount described herein is provided in one day.

In some embodiments, the peptide according to formula I is administered at an effective dose ranging from about 1-1,000 μg/kg/day (e.g., ranging from about 1-900 μg/kg/day, 1-800 μg/kg/day, 1-700 μg/kg/day, 1-600 μg/kg/day, 1-500 μg/kg/day, 1-400 μg/kg/day, 1-300 μg/kg/day, 1-200 μg/kg/day, 1-100 μg/kg/day, 1-90 μg/kg/day, 1-80 μg/kg/day, 1-70 μg/kg/day, 1-60 μg/kg/day, 1-50 μg/kg/day, 1-40 μg/kg/day, 1-30 μg/kg/day, 1-20 μg/kg/day, 1-10 μg/kg/day). In some embodiments, the peptide according to formula I is administered at an effective dose ranging from about 1-500 μg/kg/day. In some embodiments, the peptide according to formula I is administered at an effective dose ranging from about 50-500 μg/kg/day. In some embodiments, the peptide according to formula I is administered at an effective dose ranging from about 1-100 μg/kg/day. In some embodiments, the peptide according to formula I is administered at an effective dose ranging from about 1-60 μg/kg/day. In some embodiments, the peptide according to formula I is administered at an effective dose selected from about 1, 2, 4, 6, 8, 10, 15, 20, 25, 30, 35, 40, 45, 50, 75, 100, 150, 200, 250, 300, 350, 400, 450, 500, 550, 600, 650, 700, 750, 800, 850, 900, 950, or 1,000 µg/kg/day. The effective dose for a particular individual can be varied (e.g., increased or decreased) over time, depending on the needs of the individual. In some embodiments, the therapeutically effective amount described herein is provided in one dose. In some embodiments, the therapeutically effective amount described herein is provided in one day.

In some embodiments, the peptide according to formula I is administered at an effective dose from about 1-1,000 pg/kg/day (e.g., ranging from about 1-900 pg/kg/day, 1-800 pg/kg/day, 1-700 pg/kg/day, 1-600 pg/kg/day, 1-500 pg/kg/day, 1-400 pg/kg/day, 1-300 pg/kg/day, 1-200 pg/kg/day, 1-100 pg/kg/day, 1-90 pg/kg/day, 1-80 pg/kg/day, 1-70 pg/kg/day, 1-60 pg/kg/day, 1-50 pg/kg/day, 1-40 pg/kg/day, 1-30 pg/kg/day, 1-20 pg/kg/day, 1-10 pg/kg/day). In some embodiments, the angiotensin (1-7) peptide is administered at an effective dose ranging from about 1-60 µg/kg/day. In some embodiments, the angiotensin (1-7) peptide is administered at an effective dose selected from about 1, 2, 4, 6, 8, 10, 15, 20, 25, 30, 35, 40, 45, 50, 75, 100, 150, 200, 250, 300, 350, 400, 450, 500, 550, 600, 650, 700, 750, 800, 850, 900, 950, or 1,000 pg/kg/day. The effective dose for a particular individual can be varied (e.g., increased or decreased) over time, depending on the needs of the individual. In some embodiments, the therapeutically effective amount described herein is provided in one dose. In some embodiments, the therapeutically effective amount described herein is provided in one day.

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of disease.

In some embodiments, a formulation comprising a peptide according to formula I as described herein administered as a single dose. In some embodiments, a formulation comprising a peptide according to formula I as described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising a peptide according to formula I as described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising a peptide according to formula I as described herein is administered at regular intervals indefinitely. In some embodiments, a formulation comprising a peptide according to formula I as described herein is administered at regular intervals for a defined period. In some embodiments, a formulation comprising a peptide according to formula I as described herein is administered at regular intervals for 5 years, 4, years, 3, years, 2, years, 1 year, 11 months, 10 months, 9 months, 8 months, 7 months, 6 months, 5 months, 4 months, 3 months, 2 months, a month, 3 weeks, 2, weeks, a week, 6 days, 5 days, 4 days, 3 days, 2 days or a day.

Kits

The present invention further provides kits or other articles of manufacture which contains a peptide according to formula I containing the same and provides instructions for its reconstitution (if lyophilized) and/or use. Kits or other articles of manufacture may include a container, a syringe, vial and any other articles, devices or equipment useful in administration (e.g., subcutaneous, oral, by inhalation). Suitable containers include, for example, bottles, vials, syringes (e.g., pre-filled syringes), ampules, cartridges, reservoirs, or lyo-jects. The container may be formed from a variety of materials such as glass or plastic. In some embodiments, a container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may hold formulations and a label on, or associated with, the container that may indicate directions for reconstitution and/or use. For example, the label may indicate that the formulation is reconstituted to concentrations as described above. The label may further indicate that the formulation is useful or intended for, for example, subcutaneous administration. In some embodiments, a container may contain a single dose of a stable formulation containing a peptide according to formula I. In various embodiments, a single dose of the stable formulation is present in a volume of less than about 15 ml, 10 ml, 5.0 ml, 4.0 ml, 3.5 ml, 3.0 ml, 2.5 ml, 2.0 ml, 1.5 ml, 1.0 ml, or 0.5 ml. Alternatively, a container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least 1 mg/ml (e.g., at least 5 mg/ml, at least 10 mg/ml, at least 20 mg/ml, at least 30 mg/ml, at least 40 mg/ml, at least 50 mg/ml, at least 75 mg/ml, at least 100 mg/ml). Kits or other articles of manufacture may further include other materials desirable from a commercial and user standpoint, including other buffers, diluents, filters, needles, syringes, and package inserts with instructions for use. In some embodiments, kits or other articles of manufacture may include an instruction for self-administration.

The invention will be more fully understood by reference to the following examples. They should not, however, be construed as limiting the scope of the invention. All literature citations are incorporated by reference.

Uses

In some embodiments, provided peptides may be used to treat one or more diseases, disorders, or conditions. In some embodiments, the present invention provides methods of treating a disease, condition, or disorder comprising: administering to a subject in need thereof a peptide according to formula I or a composition comprising one or more such peptides. In some embodiments, the one or more peptides according to formula I is administered at an effective dose periodically at an administration interval such that at least one symptom or feature of a disease, disorder, or condition is reduced in intensity, severity, duration, or frequency or has delayed in onset.

EXEMPLIFICATION

Example 1

Stimulation of In Vitro BDNF Production

This Example shows that administration of angiotensin (1-7) peptides results in increases in BDNF production in multiple cell types.

Cell Culture Conditions

Prior to stimulation, cells were washed twice with sterile PBS and then provided with the respective serum free cell medium. Cells were incubated in the serum-free medium for one hour and afterwards stimulated for 24 hours. For the dose response measurement the peptides were used in a range from $10^{-14}$M to $10^{-6}$M. For all other experiments, a $10^{-7}$M concentration of the peptides was used, whereas isoproterenol and forskolin were used in a $10^{-6}$M concentration. To maintain the concentration of the substances over a period of 24 hours they were added again into the medium after 12 hours. After stimulation, the concentration of BDNF was determined in the cell medium. The samples were either used directly or stored at $-80°$ C.

Assay Conditions

For the determination of the concentration of BDNF the BDNF Emax® immunoassay system from Promega was used. At first, 96-well plates were coated with anti-BDNF overnight at 4° C. The next day, the plates were washed with TBST and incubated with blocking buffer for one hour at room temperature. Afterwards, the plate was washed again with TBST, and 100 µl of sample were applied per well. The plate was incubated on a shaker (~400 rpm) for two hours at room temperature and later on washed five times with TBST. To each well 100 µl pAb anti-human BDNF were added, and the plate again incubated under continuous shaking for two hours at room temperature. Thereafter, the plate was washed five times with TBST, each well applied with 100 µl anti-IgY-HRP conjugate, and incubated at room temperature with shaking for one hour. Then, the plate was washed five times with TBST and incubated for 10 min at room temperature on a shaker with TMB One Solution. The reaction was stopped with 1 M hydrochloric acid and the absorbance was measured immediately at 450 nm. The BDNF concentration was determined from a standard curve.

Figure 5:
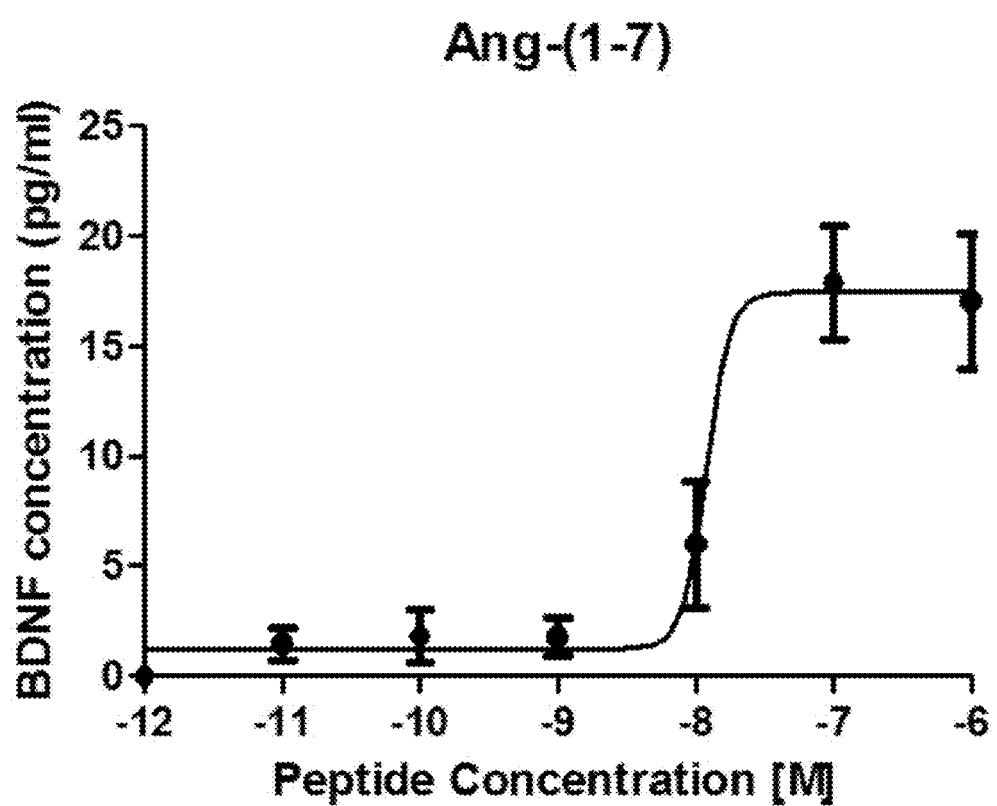
FIG. 5 shows a dose-response curve of angiotensin (1-7) and the level of BDNF stimulated at each dose in HDMEC.

Each angiotensin (1-7) peptide tested was able to stimulate significant expression of BDNF. As shown in FIGS. 1 and 5, administration of Ang (1-7) was able to stimulate significant BDNF expression in human umbilical vein endothelial cells (HUVEC) and in human dermal microvascual endothelial cells (HDMEC) at doses as low as $1\times10^{-8}$ M.

Figure 2:
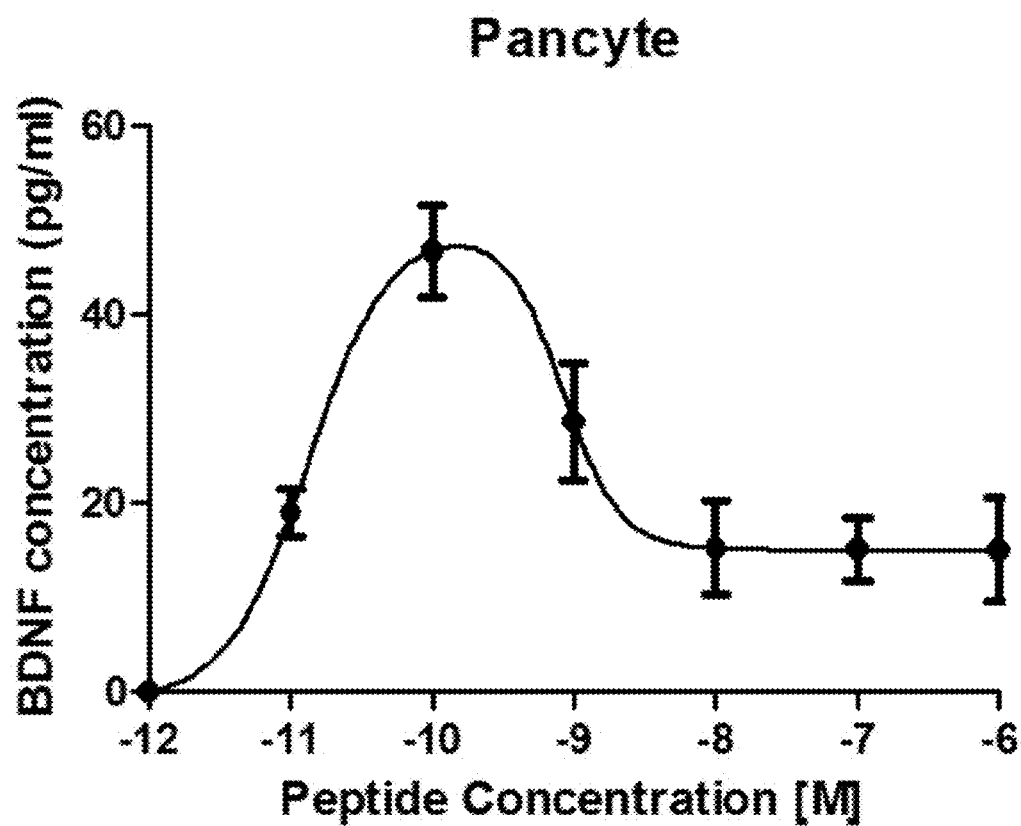
FIG. 2 depicts a dose-response curve of Pancyte and the level of BDNF stimulated at each dose in HUVEC.
Figure 6:
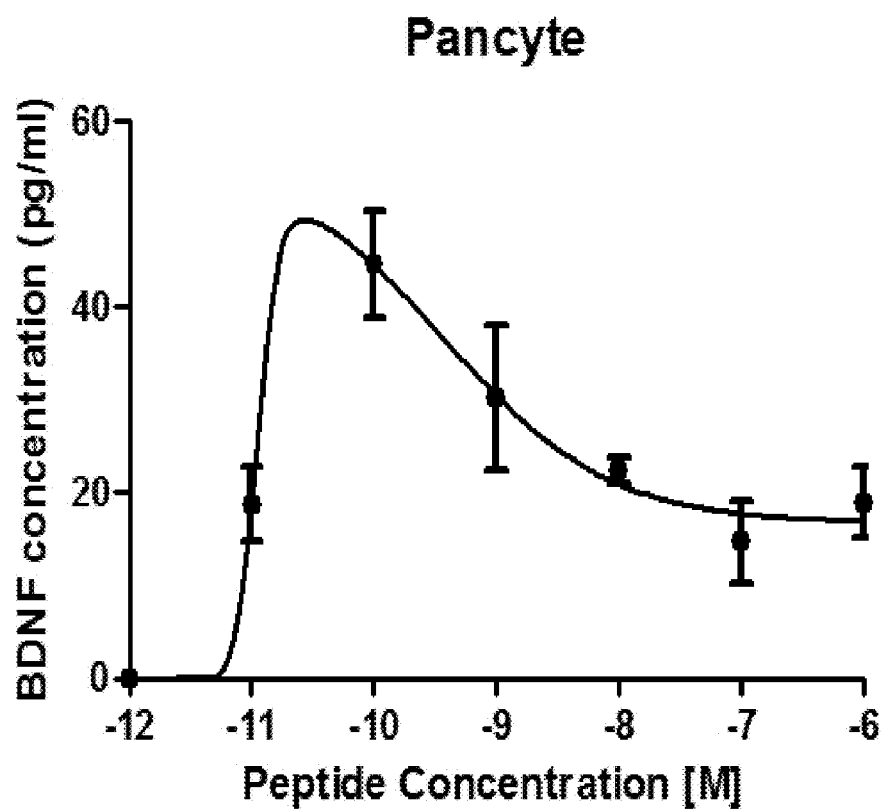
FIG. 6 depicts a dose-response curve of Pancyte and the level of BDNF stimulated at each dose in HDMEC.

As shown in FIG. 2, Pancyte was able to stimulate significant BDNF expression in HUVEC cat doses as low as $1\times10^{-11}$M. Interestingly, the largest stimulation of BDNF expression occurred at doses of Pancyte between $1\times10^{-11}$ M and $1\times10^{-9}$ M. FIG. 6 shows that Pancyte was able to stimulate BDNF expression in HDMEC at doses as low as $1\times10^{-11}$ M and that the strongest stimulation of expression was between $1\times10^{-11}$ M and $1\times10^{-9}$ M.

Figure 3:
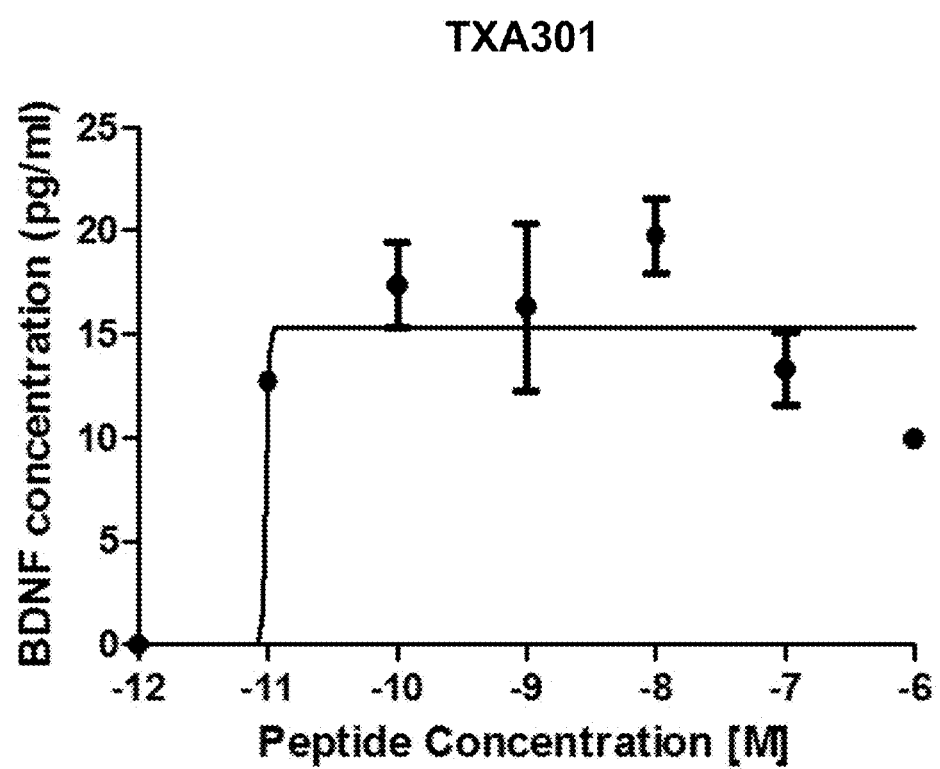
FIG. 3 shows a dose-response curve of TXA301 (SEQ ID NO: 20) and the level of BDNF stimulated at each dose in HUVEC.
Figure 7:
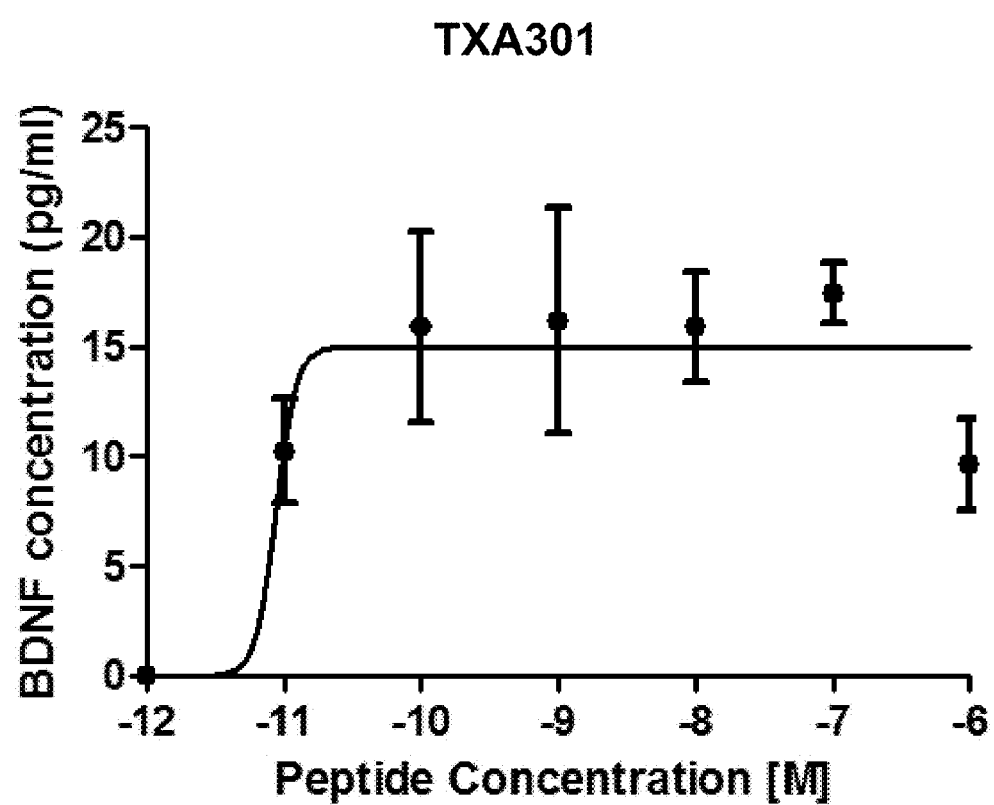
FIG. 7 shows a dose-response curve of TXA301 (SEQ ID NO: 20) and the level of BDNF stimulated at each dose in HUVEC.

TXA301 was also able to stimulate significant BDNF expression in both HUVEC and HDMEC. FIGS. 3 and 7 show that does as low as $1\times10^{-11}$ M of TXA301 were able to stimulate significant levels of BDNF expression and, interestingly, that doses 100,000 times higher than $1\times10^{-11}$ resulted in statistically similar levels of expression in both HUVEC and HDMEC.

Figure 4:
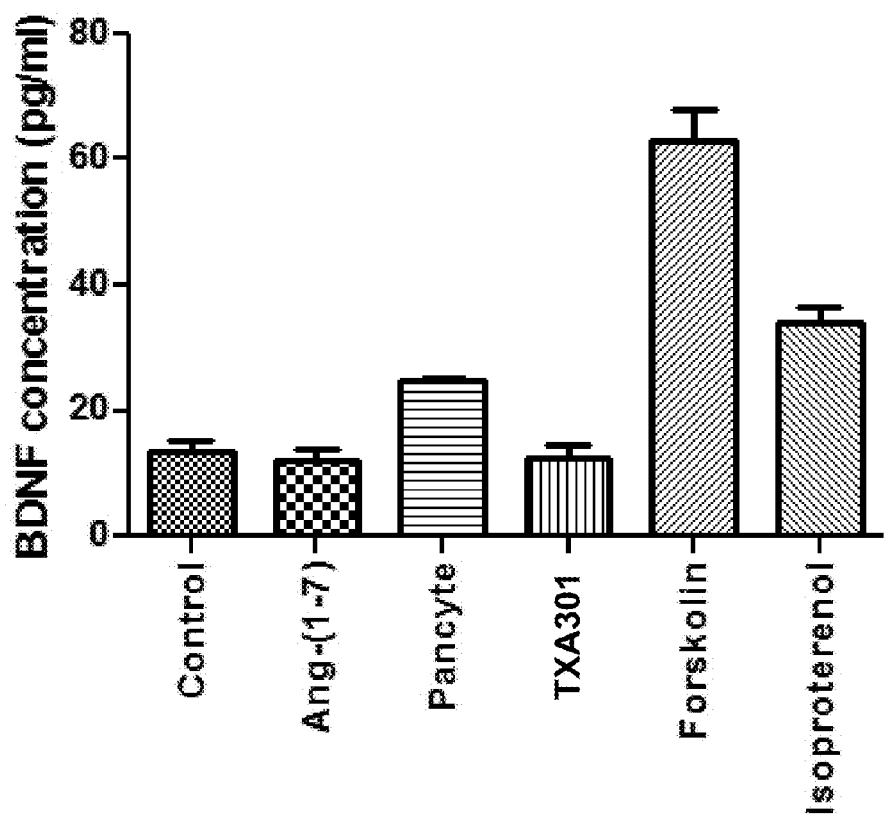
FIG. 4 shows a graph of BDNF stimulation by angiotensin (1-7), Pancyte, TXA301 (SEQ ID NO: 20), forskolin, or isoproterenol in HUVEC as compared to control.

The effect of each of Ang (1-7), Pancyte, and TXA301 on HUVEC in complete (serum-containing) medium was also examined. Additionally Forskolin and Isoproterenol were used as positive controls. As shown in FIG. 4, Pancyte was still able to stimulate BDNF above control levels, even in serum containing media.

Figure 8:
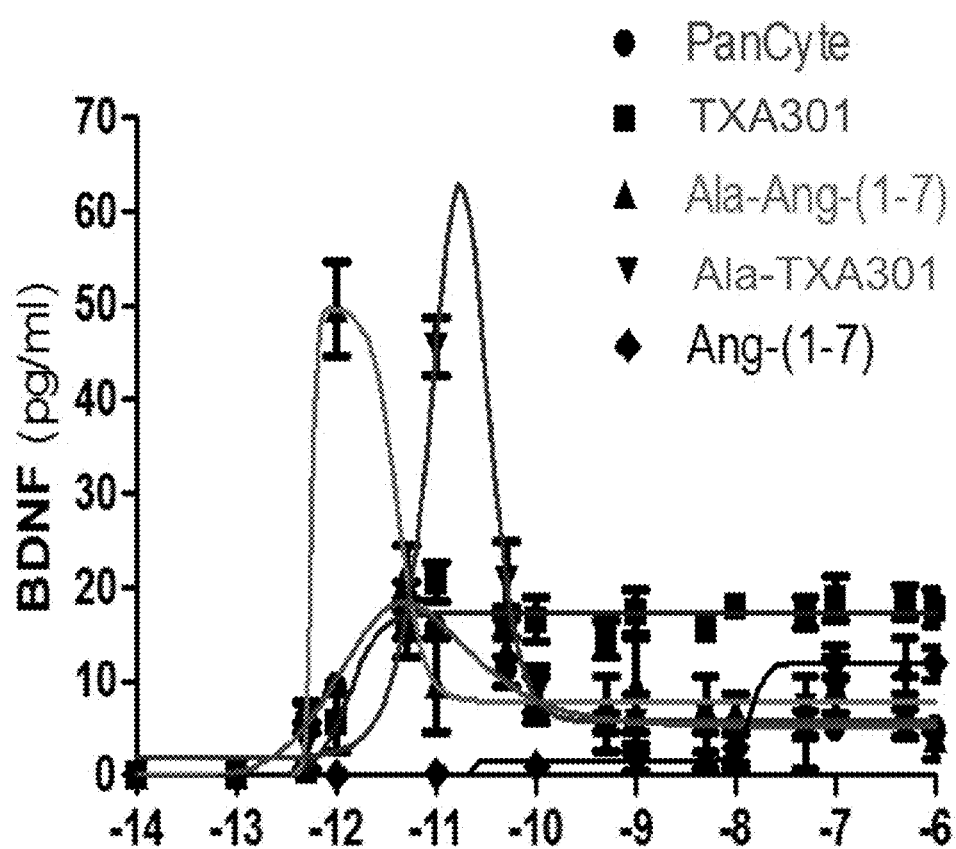
FIG. 8 shows a composite graph of the dose-response of several angiotensin (1-7) peptides including angiotensin (1-7), Pancyte, TXA301 (SEQ ID NO: 20), $Ala^1$-$Arg^2$-$Val^3$-$Tyr^4$-$Ile^5$-$His^6$-$Pro^7$ (SEQ ID NO: 17) or $Ala^1$-$Arg^2$-$Val^3$-$Ser^4$-$Ile^5$-$His^6$-$Cys^7$ (SEQ ID NO: 18, also referred to as TXA302) in HUVEC.

FIG. 8 shows a composite graph showing the data of FIGS. 1, 2, 3, 5, and 6, as well as the dose response for Ala$^1$-Arg$^2$-Val$^3$-Tyr$^4$-Ile$^5$-His$^6$-Pro' (SEQ ID NO: 17) and Ala$^1$-Arg$^2$-Val$^3$-Ser$^4$-Ile$^5$-His$^6$-Cys$^7$ (SEQ ID NO: 18) in HUVEC. As shown in FIG. 8, doses of Ala$^1$-Arg$^2$-Val$^3$-Ser$^4$-Ile$^5$-His$^6$-Cys$^7$ (SEQ ID NO: 18) between $1\times10^{-11}$ M and $1\times10^{-10}$ M and Ala$^1$-Arg$^2$-Val$^3$-Tyr$^4$-Ile$^5$-His$^6$-Pro$^7$ (SEQ ID NO: 17) between $1\times10^{-12}$ M and $1\times10^{-11}$ M were able to stimulate very high expression of BDNF as compared to all other tested peptides.

Example 2

Stimulation of In Vitro cAMP Production

Prior to stimulation with Ala$^1$-Arg$^2$-Val$^3$-Ser$^4$-Ile$^5$-His$^6$-Cys$^7$ (SEQ ID NO: 18), HUVEC cells were washed twice with PBS and then incubated for 1 hour in serum-free medium. In this Example, in order to generate a dose response curve, the peptide concentration ranged from $1\times10^{-13}$-$1\times10^{-6}$ M. After 15 minutes stimulation, the medium containing peptide was removed and the cells were lysed (0.1M HCl, 0.1% Triton X-100). The clear lysate was collected, and 25 µl were used for determining the protein concentration (Pierce BCA Protein Assay Kit, Thermo Scientific, Rockford, USA) and the remaining fraction stored at $-80°$ C. for later analysis.

cAMP concentration in cell lysates was determined using cAMP Enzyme Immunoassay Kit, Direct from Sigma-Aldrich (St. Louis, Mo., USA). Briefly, wells of 96-well plate (Goat Anti-Rabbit IgG pre-coated) were neutralized with 50 µl of Neutralizing Reagent. Next, 100 µl of acetylated cyclic AMP standard or cell lysate was added, followed by 50 µl of blue cAMP-Alkaline Phosphatase Conjugate and 50 µl of yellow EIA Rabbit Anti-cAMP antibody. The plate was then incubated on a shaker (~500 rpm) for two hours at room temperature. Next, the wells were aspirated and rinsed three times with Wash Buffer (1:10, Tris buffered saline containing detergents and sodium azide in deionized water). After the final wash the plate was tapped against clean paper towel to remove any remaining Wash Buffer. To each well 200 µl p-Nitrophenyl Phosphate Substrate Solution was added, and the plate was incubated for 1 hour at room temperature. The enzymatic reaction was stopped by adding 50 µl of Stop Solution, and the absorbance at 405 nm was measured immediately. The cAMP concentration was determined from nonlinear standard curve using GraphPad Prism 5.0 software. The final cAMP concentration was corrected against the total protein concentration.

Figure 9:
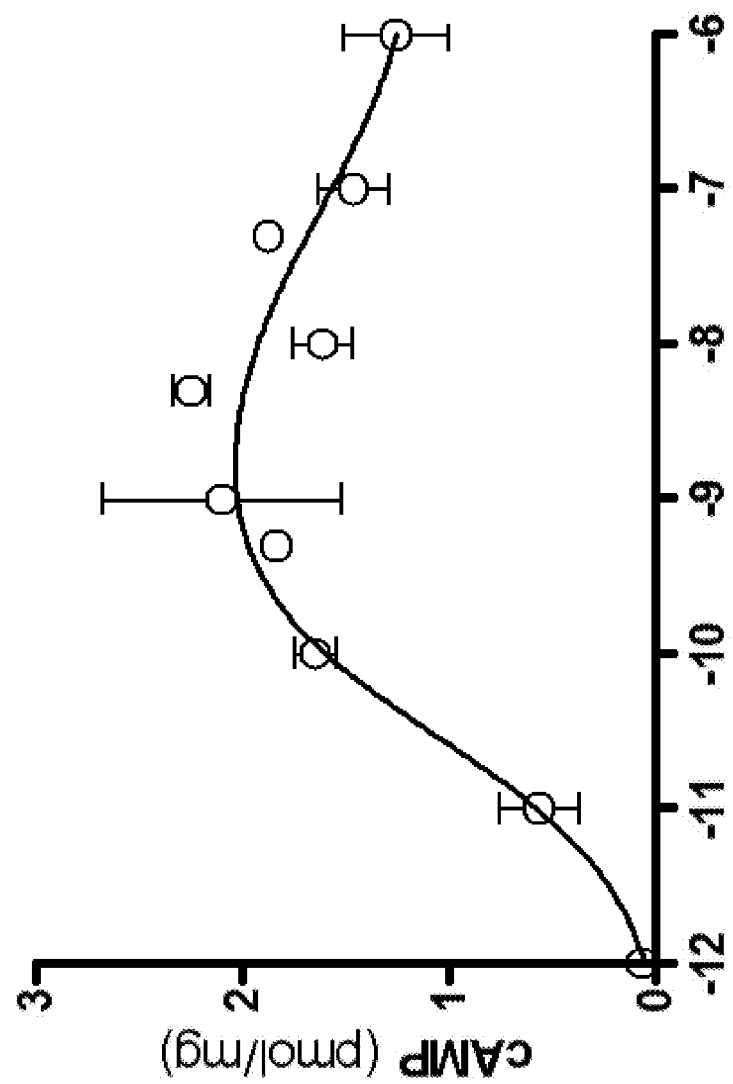
FIG. 9 shows an exemplary graph showing cAMP production by HUVEC in response to various doses of $Ala^1$-$Arg^2$-$Val^3$-$Ser^4$-$Ile^5$-$His^6$-$Cys^7$ (SEQ ID NO: 18).

As shown in FIG. 9, administration of a peptide according to SEQ ID NO: 18 resulted in a significant increase in cAMP at doses as little as $1\times10^{-11}$ M with an observed maximum, in this Example, of approximately $1\times10^{-9}$ M.

Example 3

Functional Sensorimotor Recovery Post-Stroke

In this Example, the well-accepted transient middle cerebral artery occlusion (tMCAO) rat model of stroke was used to evaluate the in vivo ability of certain provided peptides to treat and/or improve one or more functional sensorimotor symptoms of stroke. The effect of provided peptides on blood flow and vessel diameter is also assessed in this Example. As is described below, administration of provided peptides, including TXA302 (SEQ ID NO: 18), results in a surprisingly remarkable improvement in both sensorimotor function and vascular structure after a stroke.

Animal handling was performed according to guidelines of the National Institute of Health (NIH) and the Association for Assessment and Accreditation of Laboratory Animal Care (AAALAC). Animals were housed in polyethylene cages (5/cage) measuring 35×30×15 cm, with stainless steel top grill facilitating pelleted food and drinking water in plastic bottle; bedding: steam sterilized clean paddy husk (Harlan, Sani-chip cat#:2018SC+F) was used and bedding material were changed along with the cage at least twice a week. In this example, a total of 60 rats were used and each rat weighed approximately 300 grams at study initiation.

Animals were fed ad libitum a commercial rodent diet (Teklad Certified Global 18% Protein Diet cat #: 10658216). Animals had free access to acidified drinking water (pH between 2.5 and 3.5) obtained from the municipality supply according to PharmaSeed's SOP No. 214 (Water System). Animals were housed under standard laboratory conditions, air conditioned and filtered (HEPA F6/6) with adequate fresh air supply (Minimum 15 air changes/hour). Animals were kept in a climate controlled environment. Animals were kept within a temperatures range of approximately 20-24° C. with a relative humidity range of 30-70% and a 12 hours light-dark cycle. Animals were inspected on arrival and were inspected daily for any signs of morbidity or mortality. Animals found in a moribund condition and animals showing severe pain and enduring signs of severe distress (such as dyspnea, lateral recumbency, convulsions, plegia or inability to reach food or water) were humanely euthanized.

For the purposes of this Example, Transient middle cerebral artery occlusion (tMCAO) procedure Day is defined as "Day 1" in this study. On the day of surgery anesthesia were induced with 4% isoflurane in a mixture of 70% $N_2O$ and 30% $O_2$ and maintained with 1.5-2% isoflurane.

The tMCAO procedures were performed according to the method described R. Schmid-Elsaesser et al., A critical reevaluation of the intraluminal thread model of focal cerebral ischemia: evidence of inadvertent premature reperfusion and subarachnoid hemorrhage in rats by laser-doppler flowmetry, Stroke, 1998, 29(10): 2162-2170. Briefly, the right CCA (Common Carotid Artery) was exposed through a midline neck incision and carefully dissected free from surrounding nerves and fascia—from its bifurcation to the base of the skull. The occipital artery branches of the ECA (External Carotid Artery) were then isolated, and these branches were dissected and coagulated. The ECA was dissected further distally and coagulated along with the terminal lingual and maxillary artery branches, which was then divided. The ICA (Internal Carotid Artery) was isolated and carefully separated from the adjacent vagus nerve, and the pterygopalatine artery was ligated close to its origin with a 5-0 nylon suture (SMI, Belgium). Next, a 4-0 silk suture was tied loosely around the mobilized ECA stump, and a 4 cm length of 4-0 monofilament nylon suture (the tip of the suture was blunted by using a flame, and the suture was coated with polylysine, prior to insertion) was inserted through the proximal ECA into the ICA and thence into the circle of Willis, effectively occluding the MCA. The surgical wound was closed and the animals were returned to their cages to recover from anesthesia. One hour and a half after occlusion rats were re-anesthetized, the monofilament was withdrawn to allow reperfusion, the surgical wound was closed and rats were returned to their cages.

Animals were subjected to a modified Modified Neurological Rating Scale (mNRS) at 24 hours post reperfusion. Only animals with an overall score of ≥10 were included in this study. Animals were allocated into the test groups, according to the mNRS results on day 2, in order to have similar distribution of rats performance between groups. Starting on day 2, 24 hours post-surgery, each animal was administered one of 50 μg/kg of either TXA301 (SEQ ID NO: 20) or TXA302 (SEQ ID NO: 18) or 25 mg/ml in PBS; via subcutaneous (SC) administration. See Table 1 for group allocation:

TABLE 1

Group Allocation

| Group | Treatment | Dose | Administration | Treatment Duration (days) | Total Rats |
|---|---|---|---|---|---|
| 1 | Vehicle | 0 | SC | 28 | 15 |
| 2 | TXA301 | 50 μg/kg | SC | 28 | 15 |
| 3 | TXA302 | 50 μg/kg | SC | 28 | 15 |

Forelimb Placement Test (Administered Before Operation, and on Days 15, 22, 29, 36, 43 and 50)

The limb placing tests were divided into both forelimb and hindlimb tests. For the forelimb-placing test, the examiner held the rat close to a tabletop and scored the rat's ability to place the forelimb on the tabletop in response to whisker, visual, tactile, or proprioceptive stimulation. Similarly, for the hindlimb placing test, the examiner assessed the rat's ability to place the hindlimb on the tabletop in response to tactile and proprioceptive stimulation. Separate sub-scores were obtained for each mode of sensory input and added to give total scores (for the forelimb placing test: 0=normal, 12=maximally impaired; for the hindlimb placing test: 0=normal; 6=maximally impaired). Scores were given in half-point increments as follows: whisker placing (0-2), visual placing-forward (0-2), -sideways (0-2); tactile placing-dorsal (0-2), -lateral (0-2); proprioceptive placing (0-2); for a total of 0-12.

Figure 10:
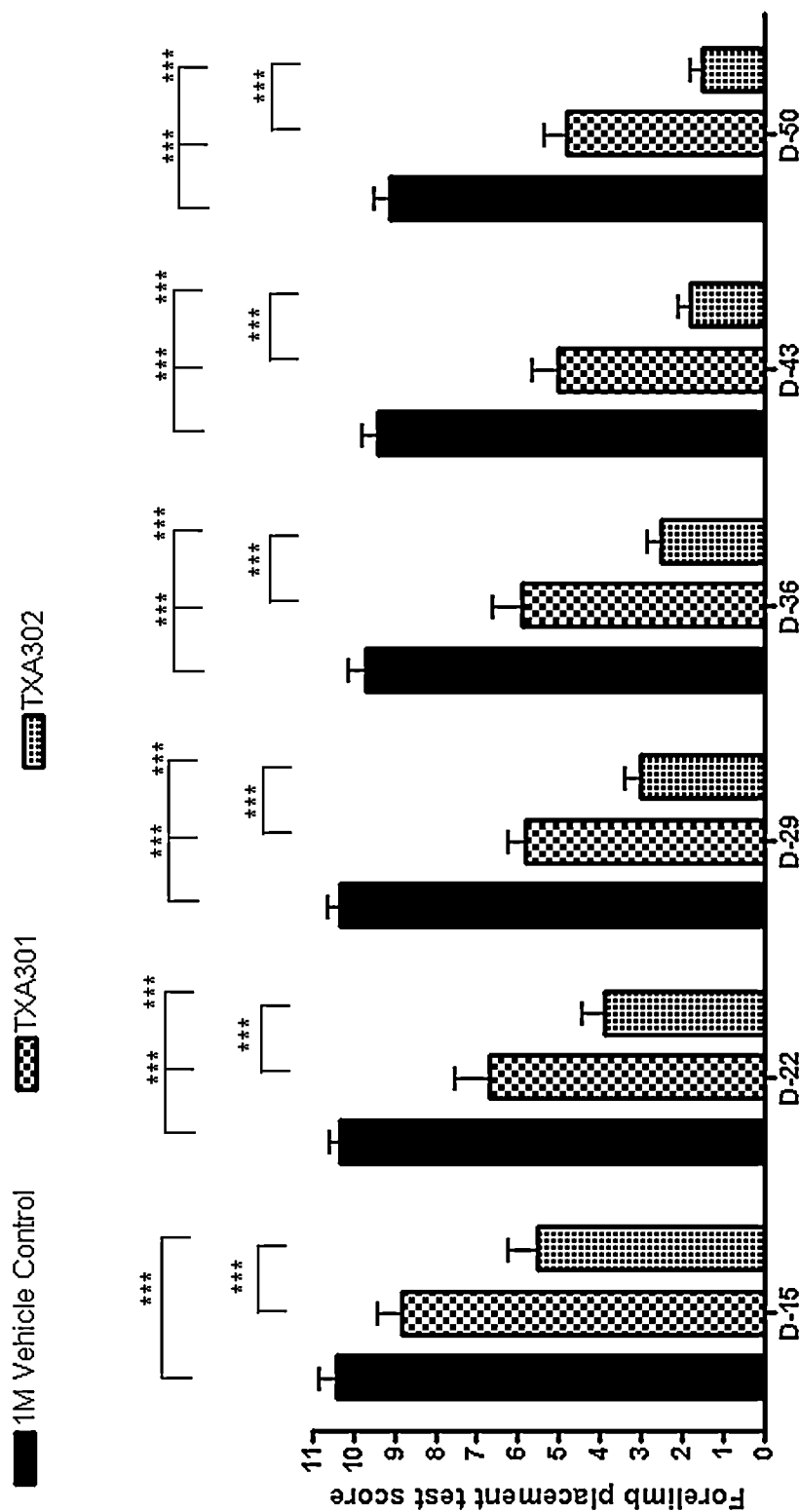
FIG. 10 shows exemplary results from a forelimb placement test from rats exposed to one of: vehicle, 50 µg/kg TXA301 (SEQ ID NO: 20), or 50 µg/kg TXA302 (SEQ ID NO: 18) given subcutaneously once per day for up to seven weeks.

FIG. 10 shows that administration of TXA302 results in a significant improvement in performance beginning on day 15, the earliest timepoint measured, as compared to vehicle control animals. While administration of TXA301 resulted in a trend toward improvement by day 15, a statistically significant effect was not achieved for this group until day 22. It is of note that by day 50, the scores in the TXA302 group had improved by more than 7 points (~78%) as compared to vehicle control animals. By comparison, the scores in the TXA301 group had improved by 4 point (~44%) in the same time period.

Stepping Test (Administered Before Operation, and on Days 15, 22, 29, 36, 43 and 50)

Animals were tested for forelimb akinesia in a stepping test. The animal was held with its hind limbs fixed with one hand and the forelimb not monitored with the other, while the unrestrained fore-paw touches a table. The number of adjusting steps were counted while the animal was moved sideways along the table surface (85 cm in approximately five seconds), in the forehand & backhand direction for both forelimbs.

Figure 11:
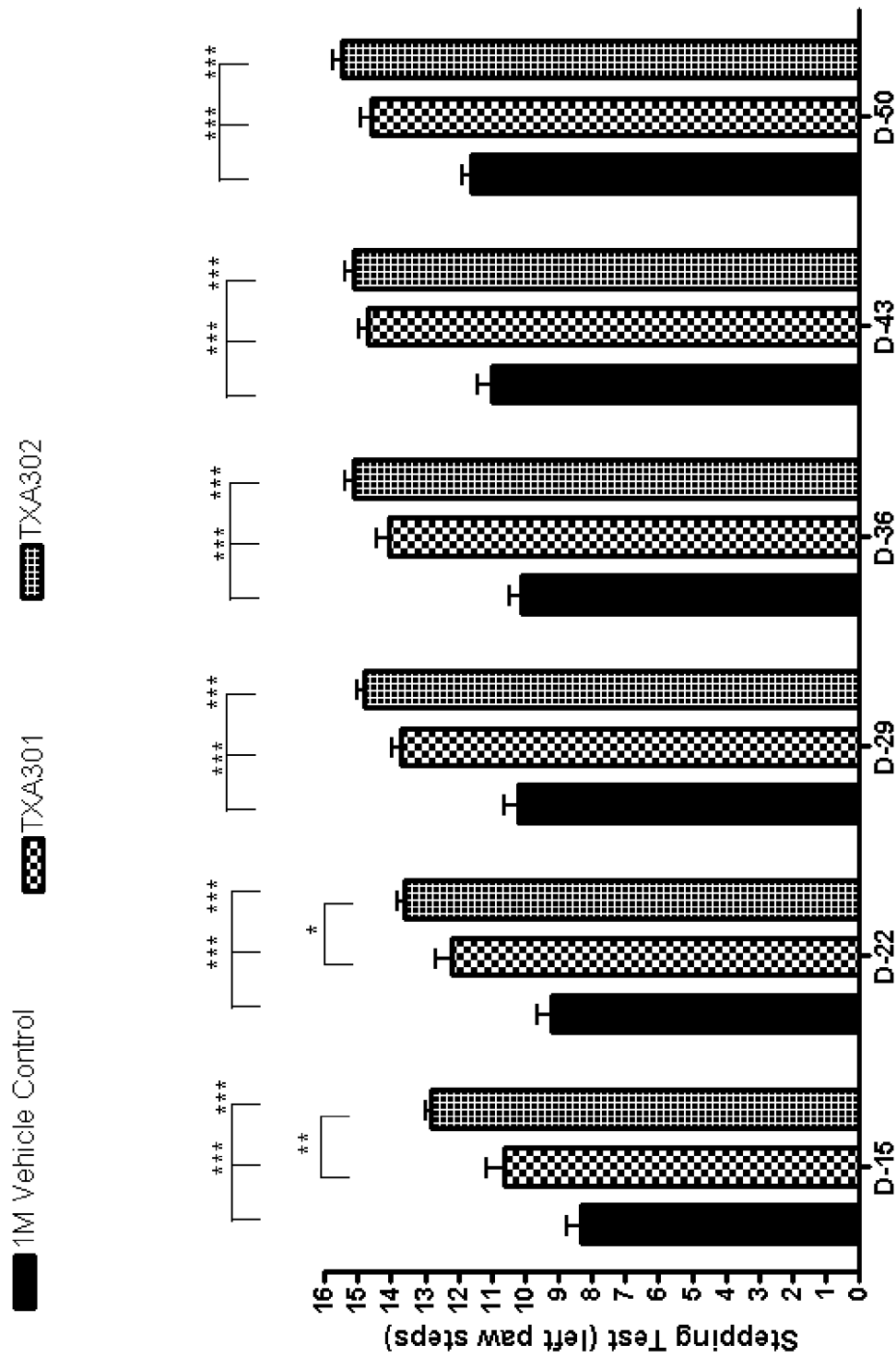
FIG. 11 shows exemplary results from a stepping test from rats exposed to one of: vehicle, 50 µg/kg TXA301 (SEQ ID NO: 20), or 50 µg/kg TXA302 (SEQ ID NO: 18) given subcutaneously once per day for up to seven weeks.

As shown in FIG. 11, rats receiving either TXA301 or TXA302 showed a statistically significant effect as early as day 15 as compared to vehicle control animals. The statistically significant effects were maintained for the duration of the study.

Body Swing Test (Administered Before Operation, and on Days 15, 22, 29, 36, 43 and 50)

The rat was held approximately one inch from the base of its tail. It was then elevated to an inch above a surface of a table. The rat was held in the vertical axis, defined as no more than 10° to either the left or the right side. A swing was recorded whenever the rat moved its head out of the vertical axis to either side. Before attempting another swing, the rat had to return to the vertical position for the next swing to be counted. Twenty (20) total swings were counted. A normal rat typically has an equal number of swings to either side. Following focal ischemia, rats tend to swing to the contralateral side (left side in this example). Body swing scores are expressed as a percentage of rightward over total swings.

Figure 12:
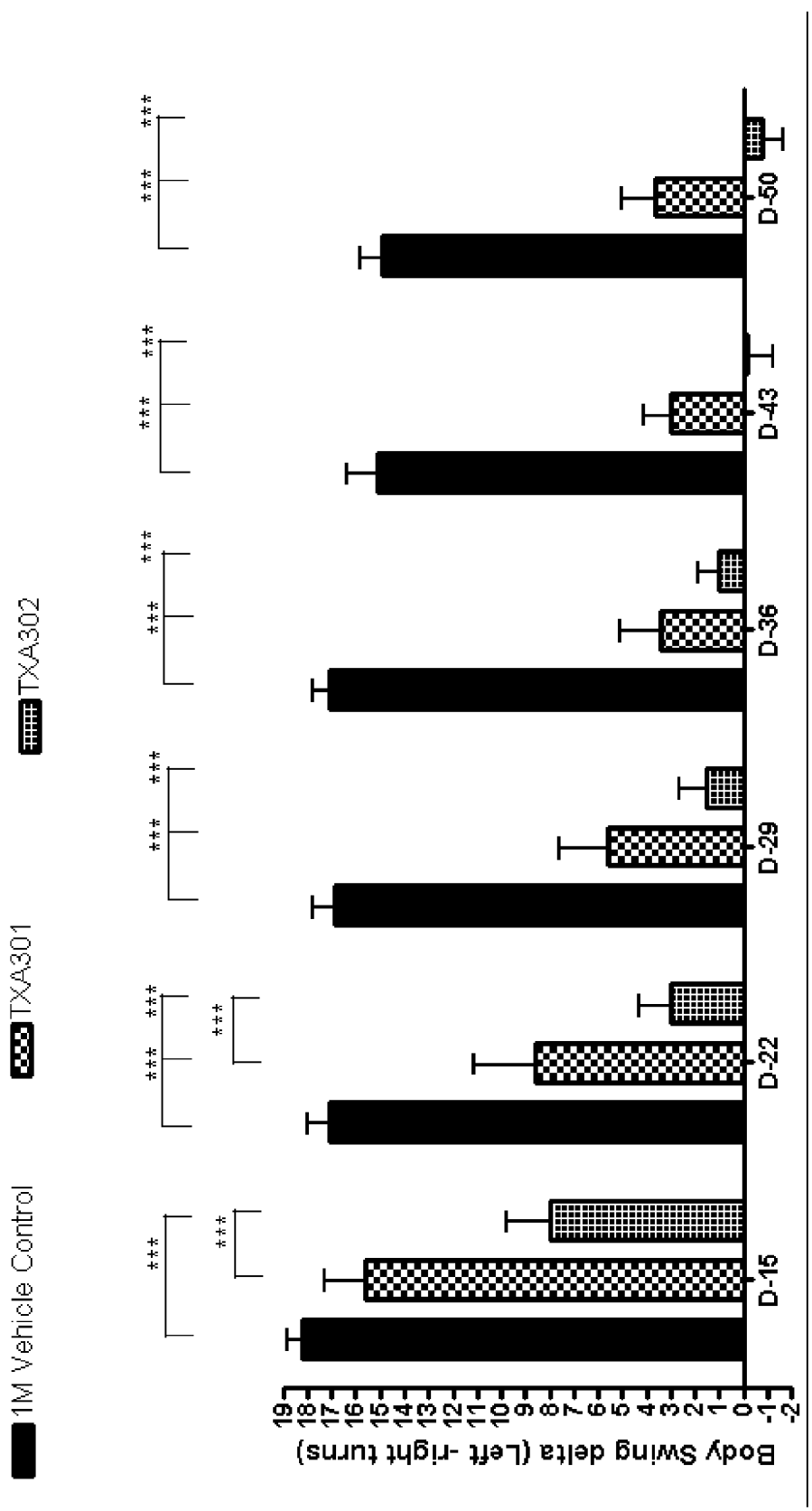
FIG. 12 shows exemplary results from a body swing test from rats exposed to one of: vehicle, 50 µg/kg TXA301 (SEQ ID NO: 20), or 50 µg/kg TXA302 (SEQ ID NO: 18) given subcutaneously once per day for up to seven weeks.

FIG. 12 shows that administration of TXA302 results in a statistically significant improvement in performance by day 15, the earliest timepoint assessed in this study, as compared to vehicle control animals. This improvement in performance of the rats in the TXA302 group was maintained throughout the rest of the study. Administration of TXA301 also resulted in a statistically significant improvement in performance, though not until day 22.

mNRS Evaluation (Administered Before Operation and on Days 2, 15, 22, 29, 36, 43 and 50)

The Modified Neurological Rating Scale (mNRS) was administered by an individual who was unaware of the drug/dose given (blind test). The mNRS as administered allows for neuro-scoring on a scale of 0 to 18 possible points. Animals with higher scores showed more severe symptoms and disability than lower scoring rats.

Figure 13:
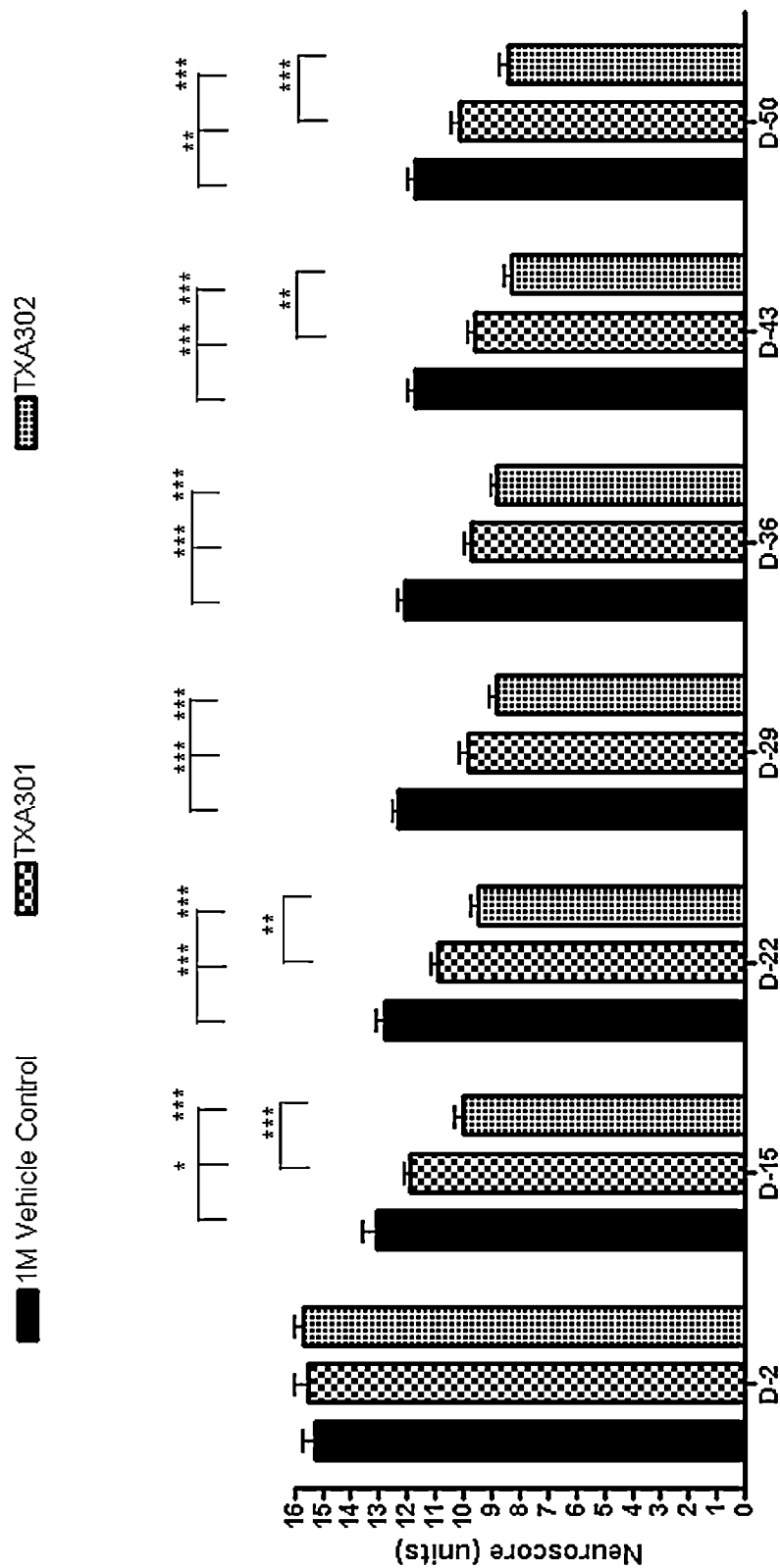
FIG. 13 shows exemplary results from a neurological scoring test from rats exposed to one of: vehicle, 50 µg/kg TXA301 (SEQ ID NO: 20), or 50 µg/kg TXA302 (SEQ ID NO: 18) given subcutaneously once per day for up to seven weeks.

As shown in FIG. 13, rats receiving either TXA301 or TXA302 showed significant increases in performance as compared to vehicle control animals as early as day 15. These improvements were maintained throughout the duration of the study.

Cerebral Blood Flow and Vessel Diameter Measurement (Day 50)

Evaluation of blood flow in the cerebral cortex and vessel constriction was carried out using a Flow-R Laser Doppler system, in which intracranial blood flow and vessels diameter (constriction/dilation) was monitored. The Doppler procedure was carried out on Day 50 after the stroke and was performed while the animals were under isoflurane anesthesia.

Figure 14:
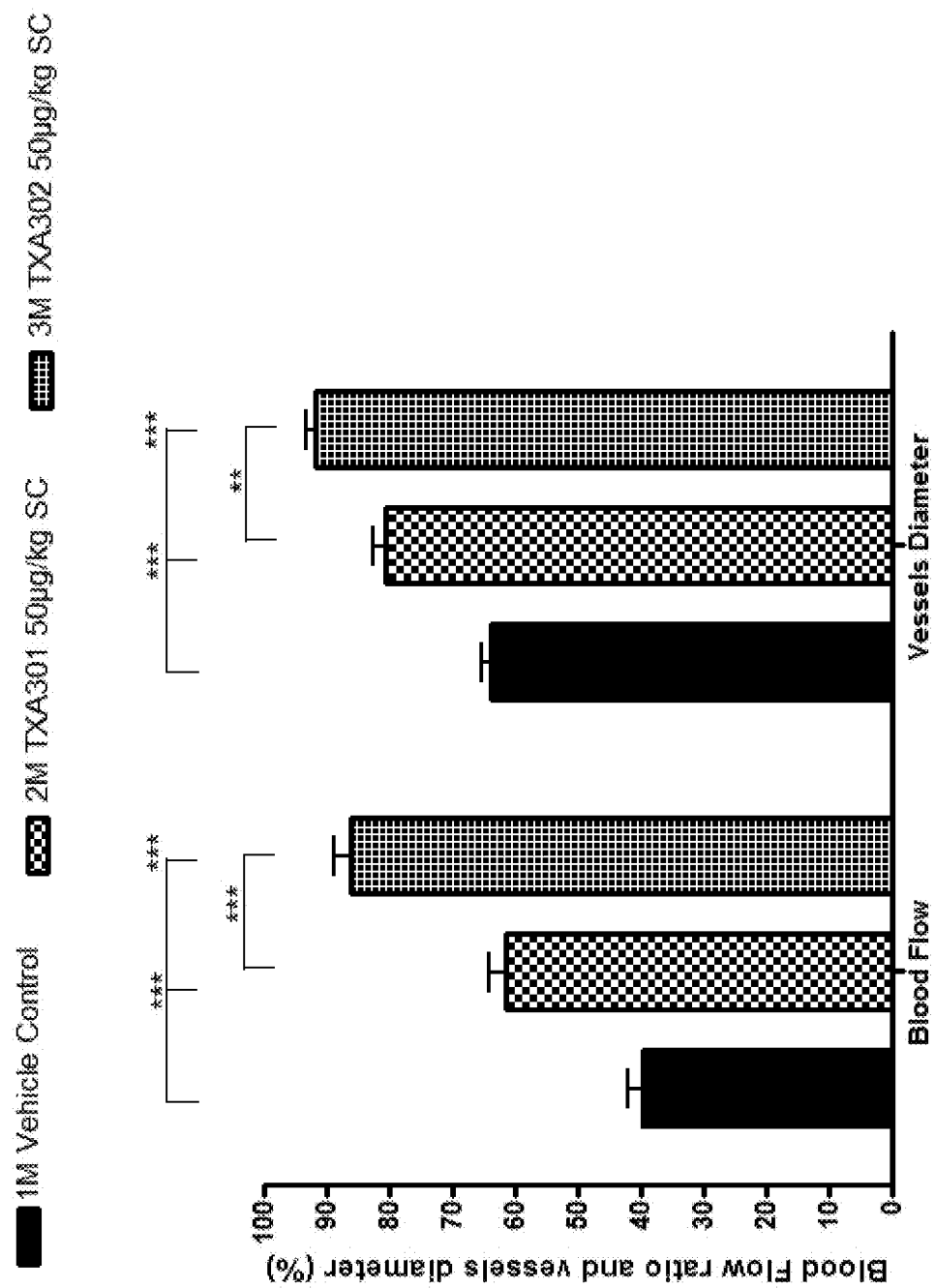
FIG. 14 shows exemplary results from a laser Doppler-based assessment of blood flow ratio (left/right %) and vessel diameter from rats exposed to one of: vehicle, 50 µg/kg TXA301 (SEQ ID NO: 20), or 50 µg/kg TXA302 (SEQ ID NO: 18) given subcutaneously once per day for up to seven weeks. Measurements were taken 49 days after a stroke event.

FIG. 14 shows that statistically significant improvement in both blood flow ratio and vessel diameter was observed by day 50 in rats treated with 50 µg/kg of either TXA301 or TXA302. Surprisingly, rats receiving TXA302 exhibited markedly improved blood flow and increased vessel diameter as compared, not only to vehicle controls, but to rats receiving TXA301 as well.

This Example shows, among other things, that administration of provided peptides, and particularly TXA302 (SEQ ID NO: 18), results in improved recovery from stroke as measured by several well-known and accepted functional sensorimotor tests as well as an assessment of blood flow and blood vessel diameter.

Equivalents and Scope

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

I claim:

1. A peptide comprising the amino acid sequence $Ala^1$-$Arg^2$-$Val^3$-$Ser^4$-$Ile^5$-$His^6$-$Cys^7$ (SEQ ID NO: 18), wherein the peptide is between 7 and 25 amino acids, inclusive.

2. The peptide of claim 1, wherein the peptide comprises one or more chemical modifications to increase protease resistance, serum stability, and/or bioavailability.

3. A pharmaceutical composition comprising a peptide according to claim 1 and a pharmaceutically acceptable carrier.

4. The pharmaceutical composition of claim 3, wherein the pharmaceutical composition is formulated for oral, intramuscular, intravenous, subcutaneous, topical, transdermal, rectal, vaginal, pulmonary, intranasal, intrabuccal, or sublingual administration.

5. The pharmaceutical composition of claim 3, wherein the pharmaceutical composition further comprises one or more pharmacologically acceptable excipients selected from a polymer carrier, a disintegration agent, a lubricant, a solvent, or a swelling agent.

6. The pharmaceutical composition of claim 3, wherein the pharmaceutical composition is formulated as a tablet, pill, capsule, granules, a syrup, a spray, an aerosol, a liposomal composition, an ointment, a suppository, an implant, a plaster, or a slow release formulation.

7. A method of treating a disease, condition, or disorder comprising:
   administering to a subject in need thereof a peptide or composition according to claim 1, wherein the disease, condition, or disorder is stroke.

* * * * *